(12) United States Patent
Williams et al.

(10) Patent No.: US 11,859,018 B2
(45) Date of Patent: Jan. 2, 2024

(54) PEPTOID-BASED CHELATING LIGANDS FOR SELECTIVE METAL CHELATION

(71) Applicant: TRIAD National Security, LLC., Los Alamos, NM (US)

(72) Inventors: Robert F. Williams, Los Alamos, NM (US); David Owen Baumann, Los Alamos, NM (US); John Cameron Gordon, Los Alamos, NM (US)

(73) Assignee: TRIAD NATIONAL SECURITY, LLC, Los Alamos, NM (US)

( * ) Notice: Subject to any disclaimer, the term of this patent is extended or adjusted under 35 U.S.C. 154(b) by 71 days.

(21) Appl. No.: 17/576,577

(22) Filed: Jan. 14, 2022

(65) Prior Publication Data

US 2022/0135623 A1     May 5, 2022

Related U.S. Application Data

(62) Division of application No. 16/596,992, filed on Oct. 9, 2019, now Pat. No. 11,254,708.

(60) Provisional application No. 62/743,147, filed on Oct. 9, 2018.

(51) Int. Cl.
   *C07K 7/54*       (2006.01)
   *A61K 47/64*     (2017.01)
   *A61K 49/00*     (2006.01)

(52) U.S. Cl.
   CPC ............... *C07K 7/54* (2013.01); *A61K 47/64* (2017.08); *A61K 49/0056* (2013.01)

(58) Field of Classification Search
   CPC ... C07K 1/06; C07K 1/00; C07K 7/02; C07K 7/54; C07K 7/50
   See application file for complete search history.

(56) References Cited

FOREIGN PATENT DOCUMENTS

WO    WO-2013192628 A1 * 12/2013 ............. A61K 38/12

* cited by examiner

*Primary Examiner* — Lianko G Garyu

(57) ABSTRACT

The present disclosure provides peptoid-based chelating ligands, corresponding cyclic peptoids, and methods of making thereof. Functional groups may be tailored for high metal binding affinity and selectivity. The side chains of a cyclic peptoid according to the present disclosure may be selected based on, for example, high affinity for actinide or other metal ions, selectivity for actinide or other metal ions, the ability to recover a metal once it is bound to the peptoid, and whether the overall peptoid should be hydrophobic or hydrophilic. Unlike siderophores, peptoid-based chelating ligands of the present disclosure are not readily hydrolyzed under physiological conditions. Therefore, peptoid-based chelating ligands may be, for example, used to treat actinide (e.g., iron and lead) poisoning in vivo. Moreover, peptoid-based chelating ligands of the present disclosure may be used for medical imaging, chelation therapy, drug delivery, and separation technologies, for example.

11 Claims, 28 Drawing Sheets

PEPTOID-BASED CHELATING LIGANDS FOR SELECTIVE METAL CHELATION

RELATED APPLICATIONS

This U.S. patent application is a Divisional patent application that claims the benefit and priority to the U.S. patent application Ser. No. 16/596,992 that was filed on Oct. 9, 2019, which further claims the benefit and priority to the Provisional Patent Application No. 62/743,147 that was filed on Oct. 9, 2018, which are incorporated herein by reference in their entirety.

FEDERALLY SPONSORED RESEARCH OR DEVELOPMENT

The United States government has rights in this invention pursuant to Contract No. 89233218CNA000001 between the United States Department of Energy (DOE), the National Nuclear Security Administration (NNSA), and Triad National Security, LLC for the operation of Los Alamos National Laboratory.

BACKGROUND

Siderophores are small organic molecules that are secreted by microorganisms to sequester bioessential Fe(III) from the environment. Due to the inherently low solubility of Fe(III), these organic molecules are exceptionally good binders for Fe(III). For example, the stability constant for the Fe(III) complex of the siderophore enterobactin, the strongest Fe(III) binder known, is $Log(K\beta)=49$.

Siderophores are exceptionally good ligands for light actinide ions such as Pu(IV) and Th(IV), and typically form complexes with these metals that are even more stable than the corresponding Fe(III) analogs. Siderophores have been implicated in the dissolution and migration of actinides within the environment, since they can mediate the dissolution of $Pu(OH)_4$ under ambient conditions.

Siderophores exhibit several inherent problems that preclude their use for actinide chelation. Since siderophores are natural products, many actinide selective functionalities and structural modifications cannot be included due to synthetic difficulties in synthesizing a rather complex natural product. Siderophores, such as enterobactin, contain a macrocyclic ester backbone that is readily hydrolyzed under physiological conditions, precluding their use as a chelating agent for treating actinide poisoning in vivo, or their use as a scavenging agent for removing actinides out of process and waste streams, which are often highly acidic.

Current treatment for actinide poisoning involves the intravenous administration of the calcium or zinc salt of trisodium diethylenetriaminepentaacetic acid (DTPA). This current therapeutic is fairly effective if given immediately after exposure, but its efficacy deteriorates over time, as actinides are incorporated into internal organs such as the liver and bones, which this drug is ineffective at removing. Side effects of this drug occur, often due to the removal of calcium and zinc, which are bioessential elements.

SUMMARY

The present disclosure provides peptoid-based chelating ligands, corresponding cyclic peptoids, and methods of making thereof. High levels of structural diversity may be achieved with cyclic peptoids. Functional groups may be tailored for high metal binding affinity and selectivity. Polymer side chains can essentially be any functionality capable of installation into the N-functionalized glycine monomer building blocks. The resulting conformation of peptoids is determined by the identity of the side chains.

The side chains of a cyclic peptoid according to the present disclosure may be selected based on, for example, high affinity for actinide or other metal ions, selectivity for actinide or other metal ions, the ability to recover a metal once it is bound to the peptoid, and whether the overall peptoid should be hydrophobic or hydrophilic.

Unlike siderophores, peptoid-based chelating ligands of the present disclosure are not readily hydrolyzed under physiological conditions. Therefore, peptoid-based chelating ligands may be, for example, used to treat actinide or other metal (e.g., iron, lead, cadmium, etc.) poisoning in vivo. Moreover, peptoid-based chelating ligands of the present disclosure may be used for medical imaging, chelation therapy, drug delivery, and separation technologies, for example.

An aspect of the present disclosure relates to a method of producing a peptoid-based chelating ligand. The method may comprise obtaining a peptoid backbone comprising a plurality of secondary amines, deprotecting at least a portion of the plurality of secondary amines, and attaching a side chain to at least a first deprotected secondary amine. Moreover, the side chain may comprise a functional group configured to form a coordinate bond with at least one hard cation. In at least some examples, the functional group is phosphonate, catecholate, amine, guanidinium, phosphoramidate, n-acylhydroxyamines, N-hydroxypyridone, or carbamoylmethylphosphine oxide (CMPO). In at least some examples, the at least one hard cation comprises at least one actinide. In at least some examples, the at least one hard cation comprises at least one lanthanide. In at least some examples, the side chain comprises at least one electron donor atom positioned between the peptoid backbone and the functional group, with the at least one electron donor atom comprising at least one of nitrogen, oxygen, or fluorine. In at least some examples, the side chain comprises at least one electron donor group comprising sulfur. In at least some examples, the at least one donor group comprising sulfur comprises at least one of a thiolate or a thiourea. In at least some examples, the method may further comprise attaching a second side chain to at least a second deprotected secondary amine, with the second side chain comprising a second function group configured to form a second coordinate bond with the at least one hard cation. In at least some examples, the method may further comprise attaching a third side chain to at least a third deprotected secondary amine, with the third side chain comprising a third function group configured to form a third coordinate bond with the at least one hard cation. In at least some examples, the at least one hard cation comprises a +3 charged actinide. In at least some examples, the at least one hard cation comprises a +3 charged lanthanide.

Another aspect of the present disclosure relates to a cyclic peptoid-based chelating ligand. The cyclic peptoid-based chelating ligand may comprise a peptoid backbone comprising a plurality of amines, and a side chain bonded to at least a first amine of the plurality of amines, with the side chain comprising a functional group configured to form a coordinate bond with at least one hard cation. In at least some examples, the functional group is phosphonate, catecholate, amine, guanidinium, phosphoramidate, n-acylhydroxyamines, N-hydroxypyridone, or carbamoylmethylphosphine oxide (CMPO). In at least some examples, the at least one hard cation comprises at least one actinide. In at least some examples, the at least one hard cation comprises at least one lanthanide. In at least some examples, the side chain comprises at least one electron donor atom positioned between the peptoid backbone and the functional group, with the at least one electron donor atom comprising at least one of nitrogen, oxygen, or fluorine. In at least some examples, the side chain comprises at least one electron donor group comprising sulfur. In at least some examples, the at least one donor group comprising sulfur comprises at least one of a thiolate or a thiourea. In at least some examples, the cyclic peptoid-based chelating ligand may comprise a second side chain bonded to at least a second amine of the plurality of amines, with the second side chain comprising a second function group configured to form a second coordinate bond with the at least one hard cation. In at least some examples, the cyclic peptoid-based chelating ligand may comprise a third side chain bonded to at least a third amine of the plurality of amines, with the third side chain comprising a third function group configured to form a third coordinate bond with the at least one hard cation. In at least some examples, the at least one hard cation comprises a +3 charged actinide. In at least some examples, the at least one hard cation comprises a +3 charged lanthanide.

BRIEF DESCRIPTION OF DRAWINGS

For a more complete understanding of the present disclosure, reference is now made to the following description taken in conjunction with the accompanying drawings.

DETAILED DESCRIPTION

Cyclic Peptoid-Based Chelating Ligands

Figure 1:
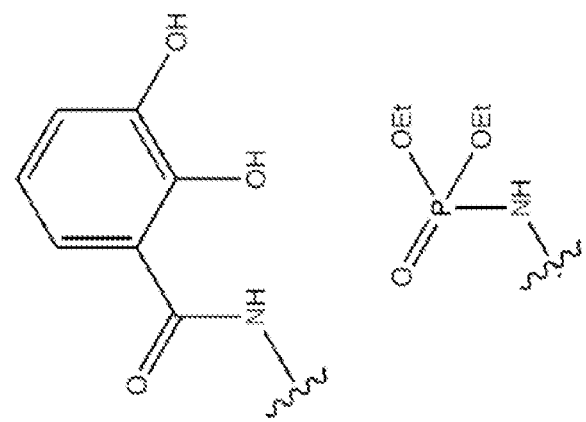
FIG. 1 shows chemical structures for an example cyclic peptoid hexamer scaffold and hard chelating groups, in accordance with embodiments of the present disclosure.
Figure 1:
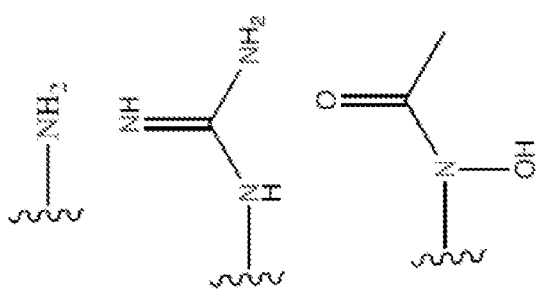
Figure 1:
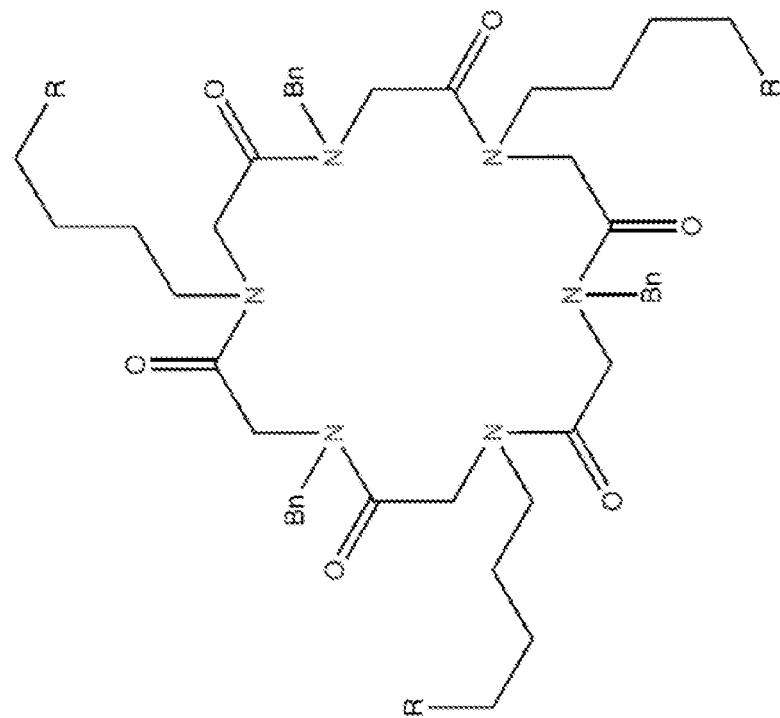

The present disclosure provides cyclic peptoid-based chelating ligands. A cyclic peptoid-based chelating ligand of the present disclosure may be produced by macrocyclization of linear peptoid sequences.

A peptoid is an N-alky or N-aryl glycine polymer having side chains appended to the nitrogen atom of the peptide backbone. This is in contrast to peptides, in which side chains are appended to α-carbons. The following are structures of generic monomers of α-peptide and α-peptoid backbones:

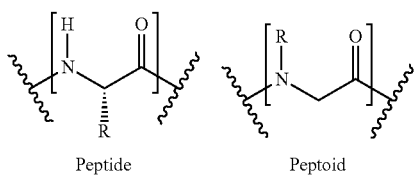

Peptide            Peptoid

Peptoids, unlike peptides, are resistant to hydrolysis under physiological conditions, thereby making peptoid-based chelating ligands of the present disclosure suitable candidates for treating metal poisoning in vivo.

A ligand is a charged or neutral functional group that binds to a central atom to form a coordination complex via a Lewis base-Lewis acid type interaction, where the ligand acts as the Lewis base, and the central atom is the Lewis acid.

Chelation is a type of bonding of ions and molecules to metal ions. More specifically, chelation involves the formation of at least two separation coordinate bonds between a polydentate ligand and a single central atom. In chelation therapy, chelating agents convert metal ions into a chemically and biochemically inert form that can be excreted.

In view of the foregoing, as used herein, a "cyclic peptoid-based chelating ligand" may refer to a cyclic N-alky or N-aryl glycine polymer having multiple side chains appended to nitrogen atoms of the peptide backbone, with the cyclic peptoid-based chelating ligand being a charged or neutral molecule that binds to a metal ion to form a coordination complex via a Lewis base-Lewis acid type interaction, whereby each of the side chains form a separate coordinate bond with the metal ion, such that the cyclic peptoid-based chelating ligand converts the metal ion into a chemically and biochemically inert form that can be excreted from a subject.

As used herein, the term "subject" may refer to a vertebrate mammal including but not limited to a human, non-human primate (e.g., monkey), mouse, rate, guinea pig, rabbit, cow, dog, cat, horse, goat, bird, reptile, or fish. A subject may be a domesticated animal, a wild animal, or an agricultural animal. Accordingly, teachings of the present disclosure may be used with respect to human and non-human subjects. For instance, teachings of the present disclosure can be used in veterinary applications (e.g., in zoos, reserves, farms, in the wild, etc.) as well as in human prevention and treatment regimens.

Peptoid Backbones

In at least some examples, a cyclic peptoid-based chelating ligand of the present disclosure may be produced from an α-peptoid (having a generic monomer as illustrated above). In at least some examples, a cyclic peptoid-based chelating ligand of the present disclosure may be produced from a β-peptoid. The following structure represents a generic monomer of a β-peptoid backbone:

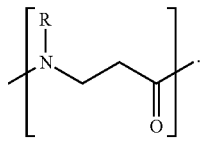

In at least some examples, a single cyclic peptoid-based chelating ligand may be produced from a hybrid system including at least one α-peptoid and at least one β-peptoid. One skilled in the art will appreciate that achievable ring sizes and conformations may depend on the α-peptoid(s) and/or β-peptoid(s) used.

Solid phase peptoid synthesis can be used to produce linear peptoids from suitably produced monomers that have variable side chains with variable functional groups. Solid phase peptoid synthesis may include acylating a secondary amine, on a resin, by an activated haloacetic acid, such as bromoacetic acid, with N.N-diisopropylcarbodimide (DIC). One skilled in the art will appreciate that multiple resins with multiple coupling chemistries and protecting groups can be used for synthesis of a linear peptoid to achieve the optimal yield of desired peptoid. For example, the solid phase synthesis of a linear hexa-peptoid can be accomplished using a bromoacetic acid functionalized 2-Chlorotrityl resin [loading 200-400 mesh polystyrene 1% DVB cross linking]. A Biotage Alstra microwave-assisted peptide synthesizer or other similar peptide synthesizer can be used for automated synthesis. Initial displacement of the bromide of the functionalized resin adds the first peptoid and then the peptoid chain is elaborated by iterative coupling with successive functionalized monomers using an activation catalyst to accelerate the coupling reaction. Once the linear peptoid has been constructed, protecting groups on the functional groups of the peptoid side chains are removed, and then the completed linear peptoid can be removed from the resin. The peptoid can be purified by chromatography and analyzed prior to cyclization into the cyclic peptoid.

Peptoid Cyclization

In at least some examples, a string of peptoid monomers (that have yet to be modified to include side chains having hard chelating groups) may be cyclized to produce a cyclic peptoid scaffold upon which side chains (having hard chelating groups) may be appended. Such cyclic peptoid scaffolds may be produced via macrocyclization with peptoid coupling reagents, or cyclized on a resin solid support.

Cyclization of a typical linear hexamer to cyclic hexamer can be accomplished using a variety of coupling reagents under conditions of high dilution ($10^{-3}$ M). Typically, cyclizations using PyBrOP were found to be low yielding and the resulting product is very difficult to separate from reaction by products. Just switching solvents from $CH_2Cl_2$ to DMF still resulted in extremely low yields. Both PyClock and MSNT mediated cyclizations showed improved yields; however, cyclizations using HATU were found to be high yielding and could be scaled to 100 mg quantities of starting material to give the cyclic product in about 75% yield.

FIG. 1 illustrates an example of a cyclic peptoid hexamer scaffold and hard chelating groups in accordance with the present disclosure. One skilled in the art will appreciate that cyclic peptoid scaffolds of the present disclosure may be of various ring sizes, such as detailed elsewhere herein. As illustrated in FIG. 1, a cyclic peptoid hexamer scaffold (chemical structure on the left side of FIG. 1) of the present disclosure may include one or more side chains functionalized with chelating, anchoring, and/or polarity modifying groups bearing hard chelating groups favoring hard cation binding. Such substitution is described elsewhere herein.

In at least some other examples, a string of peptoid monomers (that have already been modified to include side chains having hard chelating groups) may be synthesized with appropriate protecting groups on the hard chelating groups using either solid phase or solution synthesis to produce variously functionalized peptoids that can be cyclized as described herein to produce a cyclic peptoid-based chelating ligand after removal of the protecting groups. Alternatively, as one skilled in the art will appreciate, a peptoid with a protected functional group, such as an amine, alcohol, thiol, etc. or such as a halogen, acid, ester, etc., can be synthesized and cyclized. After removal of the protecting group, the desired binding functionality, such as a catecholate, phosphine, phosphate, amine, imine, amidine, guanidine, or aromatic hard ligand can be attached to the cyclic peptoid scaffold to tune desired binding properties.

Ring Size

Cyclic peptoid-based chelating ligands of the present disclosure may be of various ring sizes. Such various ring sizes enables selective chelation of various metal cations. A ring size of a cyclic peptoid-based chelating ligand of the present disclosure is determined by the number of glycine monomers incorporated into a linear peptoid scaffold. Ring sizes for the peptoid scaffold can vary from 4 to 9. However, synthesis yields may be affected as the ring contracts below 5 and expands to 8 or more. The nitrogens in the cyclic peptoid ring can also participate in the binding of metals in concert with the hard ligand binders that are located on the peptoid side chains, and by altering the ring size and the ligands one skilled in the art will appreciate that different size metal complexes can be preferentially bound with high affinity allowing the cyclic peptoid to select one metal complex in preference to another. A smaller ring can bind sodium in preference to potassium or cesium or iron while a larger ring can bind iron or copper in preference to ruthenium or iridium, which would require an even larger ring and/or modified ligand groups. Lanthanides and actinides, since they are larger, may require hexameric or larger ring systems for enhanced binding.

Side Chains

Cyclic peptoid-based chelating ligands of the present disclosure may be designed to be selective for various metal cations. As such, cyclic peptoid-based chelating ligands of the present disclosure may be useful in chelation therapy of various metals. Generally, selective binding of specific metal cations may be achieved by careful choice of the hardness of the Lewis basic site(s), linker length, ring size, and conformation dictated by the identity of all incorporated side chains.

As described above, a string of peptoid monomers (that have yet to be modified to include side chains having hard chelating groups) may be cyclized to produce a cyclic peptoid scaffold. Post-cyclization, the cyclic peptoid scaffold may include one or more nitrogen atoms having side chains (e.g., benzyl (Bn) side chains) bound thereto. The side chains of the cyclic peptoid scaffold may be deprotected and modified with one or more different side chains having the same or different hard chelating groups.

A cyclic hexamer with a protecting group, such as a CBZ group, can be deprotected by reduction over Pd/C by heating to reflux until the reduction is complete (about 1 hr or determined to be complete by mass spectrometric analysis). After addition of formic acid dropwise by syringe, the reaction mixture may be refluxed with stirring for another hour until mass spectroscopy indicates complete conversion to the triamine. Thereafter, the mixture may be filtered. The solid may be dissolved in aqueous HCl, frozen in liquid nitrogen, and lyophilized to produce a deprotected cyclic peptoid amine as an HCl salt in 95% yields. One skilled in the art will appreciate that the method of deprotection may be varied depending on the type of protecting group. For example deprotection to the linear peptoid side chains and removal from the resin support can be accomplished by reaction with trifluoroacetic acid and reagents specific to the chosen protecting group.

Side chains may be chosen with respect to chain linker length, ligand type (e.g., degree of hardness), desired solubility of the cyclic peptoid-based chelating ligand, desired bioavailibliity of the cyclic peptoid-based chelating ligand, etc. In at least some examples, one or more side chains may be selected to serve as an anchor(s) to a solid support.

In at least some examples, a side chain may include one or more hard chelating groups selective for one or more f-block elements. F-block elements consist of lanthanides and actinides, which are also known as the inner transition elements.

Lanthanides are a series of fifteen metallic chemical elements from atomic number 57 to atomic number 71 in the periodic table. The fifteen lanthanides are lanthanum (La, atomic number 57), cerium (Ce, atomic number 58), praseodymium (Pr, atomic number 59), neodymium (Nd, atomic number 60), promethium (Pm, atomic number 61), samarium (Sm, atomic number 62), europium (Eu, atomic number 63), gadolinium (Gd, atomic number 64), terbium (Tb, atomic number 65), dysprosium (Dy, atomic number 66), holmium (Ho, atomic number 67), erbium (Er, atomic number 68), thulium (Tm, atomic number 69), ytterbium (Yb, atomic number 70), and lutetium (Lu, atomic number 71).

Actinides are a series of fifteen metallic elements from atomic number 89 to atomic number 103 in the periodic table. The fifteen actinides are actinium (Ac, atomic number 89), thorium (Th, atomic number 90), protactinium (Pa, atomic number 91), uranium (U, atomic number 92), neptunium (Np, atomic number 93), plutonium (Pu, atonic number 94), americium (Am, atomic number 95), curium (Cm, atomic number 96), berkelium (Bk, atomic number 97), californium (Cf, atomic number 98), einsteinium (Es, atomic number 99), fermium (Fm, atomic number 100), mendelevium (Md, atomic number 101), nobelium (No, atomic number 102), and lawrencium (Lr, atomic number 103).

In at least some examples, one or more hard chelating groups may be selected based on one or more of high affinity for a lanthanide(s), actinide(s), or other metal cation(s); selectivity for a lanthanide(s), actinide(s), or other metal cation(s); an ability to recover a metal cation once the metal cation is bound to a cyclic peptoid-based chelating ligand; and/or whether the overall cyclic peptoid-based chelating ligand should be hydrophobic or hydrophilic.

Typical hard chelating ligands that are specific for lanthanide and actinide binding include catecholates, phosphoramidates, amidines, and guanidines. Since the size of the metal ion affects it's binding to the cyclic peptoid, the ring size and length of the tether between the ring and the hard chelating ligand can be tuned to provide optimal binding to the specific metal that is targeted. If a cyclic peptoid is to be used for treatment of metal poisoning, the goal is to remove the metal from the biological regime as rapidly as possible;

consequently, the binding to the target metal must be as tight as possible so the metal is not released during the removal process. However, if the purpose is to separate a metal from other metals then, after it has been sequestered, the cyclic peptoid binding must be selective but not high enough that release after removal is prevented.

Replacement of some of the side chains on the cyclic peptoid can be used to adjust the hydrophobicity or hydrophilicity of the cyclic peptoid complex. For example, cadmium and some radionuclides can be accumulated into lipid structures in the body, rendering normal chelation therapy inaffective in removing metal ions. By adding lipid like hydrocarbon side chains and aromatic groups, the cyclic peptoid will be better able to remove lipid soluble metal complexes. Contrarily, a side chain on the cyclic peptoid can be constructed with hydroxyl, amine, or carboxylic groups to make the overall complex more hydrophilic and water soluble to achieve a better separation of aqueous soluble actinides.

Various hard chelating groups may be incorporated into a cyclic peptoid-based chelating ligand that is selective for one or more actinides and/or one or more lanthanides. Example actinide(s) and/or lanthanide(s) selective hard chelating groups include, but are not limited to, phosphonate (C—PO(OH)$_2$ or C—PO(OR)$_2$, where R is alkyl or aryl), catecholate ($C_6H_4O_2$), amine (either a primary amine, secondary amine, or tertiary amine), guanidinium ($CH_6N_3^+$), phosphoramidate ($H_2NO_3P^{-2}$), n-acyl derivatives of hydroxyamines ($H_3NO$), n-hydroxypyridones ($C_5H_5NO_2$ being the molecular formula for hydroxypyridone), and carbamoylmethylphosphine oxide (CMPO).

A cyclic peptoid may be tuned to be selective for one or more particular actinides and/or lanthanides by changing the size of the cyclic peptoid and/or the ligand groups. For example, instead of having three of the same hard ligands (such as tricatacholate), a cyclic peptoid complex can be constructed with one, two, or three catecholates and one or two amidines or guanidines to change the selectivity for the various lanthanides and actinides. For example, gadolinium is bound tightly by the carboxylic acids of DOTA and other lanthanides can be selected by altering the number of carboxylic acids used to bind the metal.

Cyclic peptoid-based chelating ligands of the present disclosure may be of various hardnesses to enable chelation of various elements. In at least some examples, one or more hard atoms [e.g., one or more hard electron donor atoms such as nitrogen (N, atomic number 7), oxygen (O, atomic number 8), and fluorine (F, atomic number 9)] may be positioned between a peptoid backbone and a hard chelating group of a side chain. An electron-donating hard atom may increase the affinity of a hard chelating group for a hard cation, such as a trivalent lanthanide (having a +3 charge), trivalent actinide (having a +3 charge), and/or cations of transition metals and main group elements.

In general, the harder the chelating group, the tighter the binding to the metal cation can be. Consequently, by reducing the hardness of the chelator (e.g., by adding additional functional groups that are soft electron donors), the extend of binding can be tuned to the target metal complex.

In at least some examples, a side chain may be modulated with one or more soft electron donors. Examples of soft electron donors include thiolates and thioureas. A thiolate ($RS^-$) is a derivative of a thiol (an organic compound containing the group —SH) in which a metal atom replaces the hydrogen attached to sulfur. A thiourea is an organosulfur compound with the formula $SC(NH_2)_2$. Modulating one or more side chains of a cyclic peptoid-based chelating ligand may enable the cyclic peptoid-based chelating ligand to be used as a lead scavenger in medical applications, as well as be used for precious metal recovery.

A cyclic peptoid-based chelating ligand of the present disclosure may be configured such that the cyclic peptoid-based chelating ligand has a number of hard chelating groups corresponding to a charge of a metal cation to be bound by the cyclic peptoid-based chelating ligand. For example, a cyclic peptoid-based chelating ligand for binding a +3 metal cation may have three hard chelating groups, a cyclic peptoid-based chelating ligand for binding a +4 metal cation may have four hard chelating groups, a cyclic peptoid-based chelating ligand for binding a +5 metal cation may have five hard chelating groups, etc.

Side chain length may be varied to select for certain sizes of metal cations. As the size of the metal cation increases, so may the cavity of the cyclic peptoid that will accommodate the metal cation. Consequently, small metal cations may be accommodated best with side chain lengths of n=2-4, and larger metal cations may be accommodated best with side chain lengths of n=4-8 or more.

Administration of Peptoid-Based Chelating Ligand

In connection with the treatment of metal poisoning, in vivo, the peptoid-based chelating ligands of the present disclosure may be introduced systemically to a patient having, or suspected of having, metal poisoning. The peptoid-based chelating ligands may preferably be introduced systemically, although localized administration may be appropriate in some circumstances (e.g., in the case of localized metal poisoning). The peptoid-based chelating ligands may be formulated for oral, topical, or rectal administration using well-known formulation methodologies. Additionally, when formulated in a physiologically acceptable buffer solution, the peptoid-based chelating ligands may be introduced parenterally (e.g., intravenously or by injection). The determination of effective therapeutic levels, and the formulations required to deliver such effective therapeutic levels, are determined on a case-by-case basis which is dependent, for example, on the extent of the metal poisoning to be treated. Such determinations are readily made by one skilled in the art using no more than routine experimentation.

While biological model system data is not provided herein, one skilled in the art will appreciate that siderophores, like enterobactin, show extremely high binding to iron under physiological conditions. Unfortunately, enterobactin is readily hydrolyzed and rendered inactive. The peptoid backbone of the present disclosure, in at least some examples, is similar to the peptide backbone of enterobactin, but is resistant to hydrolysis and has been successfully used in construction of successful drugs. Consequently, there is a high degree of certainty that cyclic peptoids of the present disclosure will be physiologically effective and safe for chelation therapy. Additionally, cyclic peptoid of the present disclosure, in addition to being effective in chelation therapies, also have the potential as contrast agents for medical imaging, as targeted delivery mechanisms for radiotherapy applications, and as highly specific tools for separating actinides and other metals.

EXAMPLES

The following reagents were used as supplied by the manufacturer unless otherwise noted. Reactions, except for TFA deprotections of t-butyl esters were performed under argon (Ar). Flash chromatography was performed on a Biotage Isolera instrument. Products were typically dried under high vacuum (about 1×10⁻² mm Hg) overnight. Silica TLC plates were visualized via ceric ammonium molybdate, phosphomolybdic acid or $I_2$ stain.

t-BuO₂CCH₂NHCH₂Ph

Figure 2:
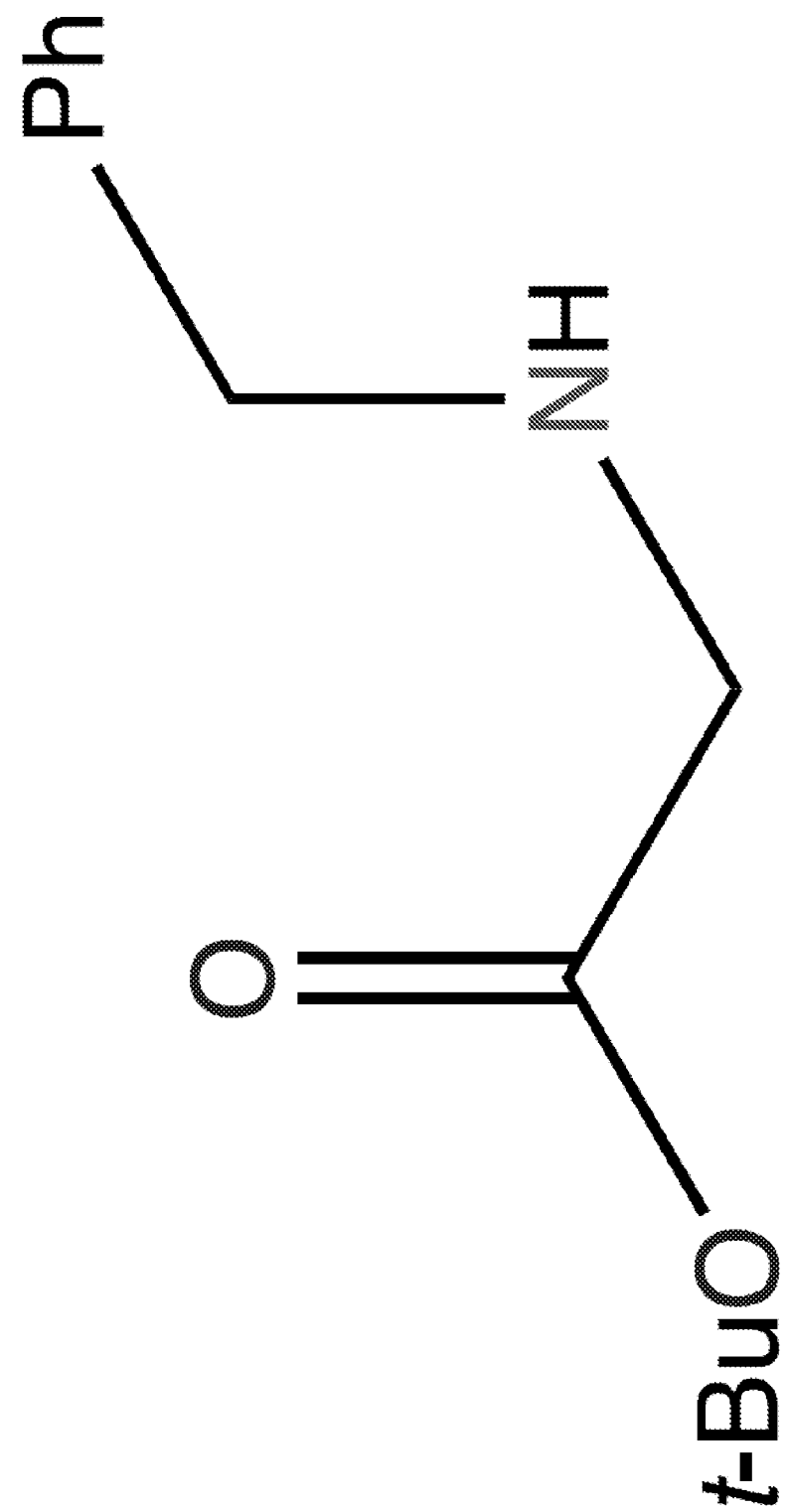
FIG. 2 shows a chemical structure of an example peptoid monomer, in accordance with embodiments of the present disclosure.

FIG. 2 illustrates the chemical t-BuO₂CCH₂NHCH₂Ph, which may be used as a starting peptoid monomer for a backbone of a cyclic peptoid-based chelating ligand of the present disclosure. One skilled in the art will appreciate that t-BuO₂CCH₂NHCH₂Ph is merely illustrative, and that other peptoid monomers may be used in accordance with the present disclosure.

To produce t-BuO₂CCH₂NHCH₂Ph, triethylamine (about 13 mL, about 93.3 mmol, 1.0 eq.) was added to a solution of benzylamine (about 10.2 mL, about 93.3 mmol, 1.0 eq.) in N,N-dimethylformamide (DMF) (about 60 mL) contained in a round bottomed flask (RBF) (e.g., a 250 mL RBF). After chilling to 0° C. in an ice bath, a solution of t-butyl bromoacetate (about 12.4 mL, about 84.0 mmol, 0.9 eq.) in DMF (about 33 mL) was added dropwise (e.g., through an addition funnel). The initial concentration of t-butyl bromoacetate after the addition was about 0.5 M. The reaction mixture was warmed to room temperature (rt) after stirring for about 0.5 hr at about 0° C. The resulting reaction mixture was stirred for about 3 hours at room temperature (rt), diluted with water (H₂O) (about 200 mL) and extracted with ethyl acetate (EtOAc) (about 100 mL, 2×50 mL). The combined organic phase was washed with brine (about 100 mL), dried (e.g., over sodium sulfate (Na₂SO₄)), filtered, and concentrated. The resulting oil was dried under high vacuum overnight. The crude product was purified by EtOAc/hexane flash chromatography on silica and dried under high vacuum, yielding about 13.7 g t-BuO₂CCH₂NHCH₂Ph as an oil (about 74% yield).

t-BuO₂CCH₂NFMOC(CH₂Ph)

Figure 3:
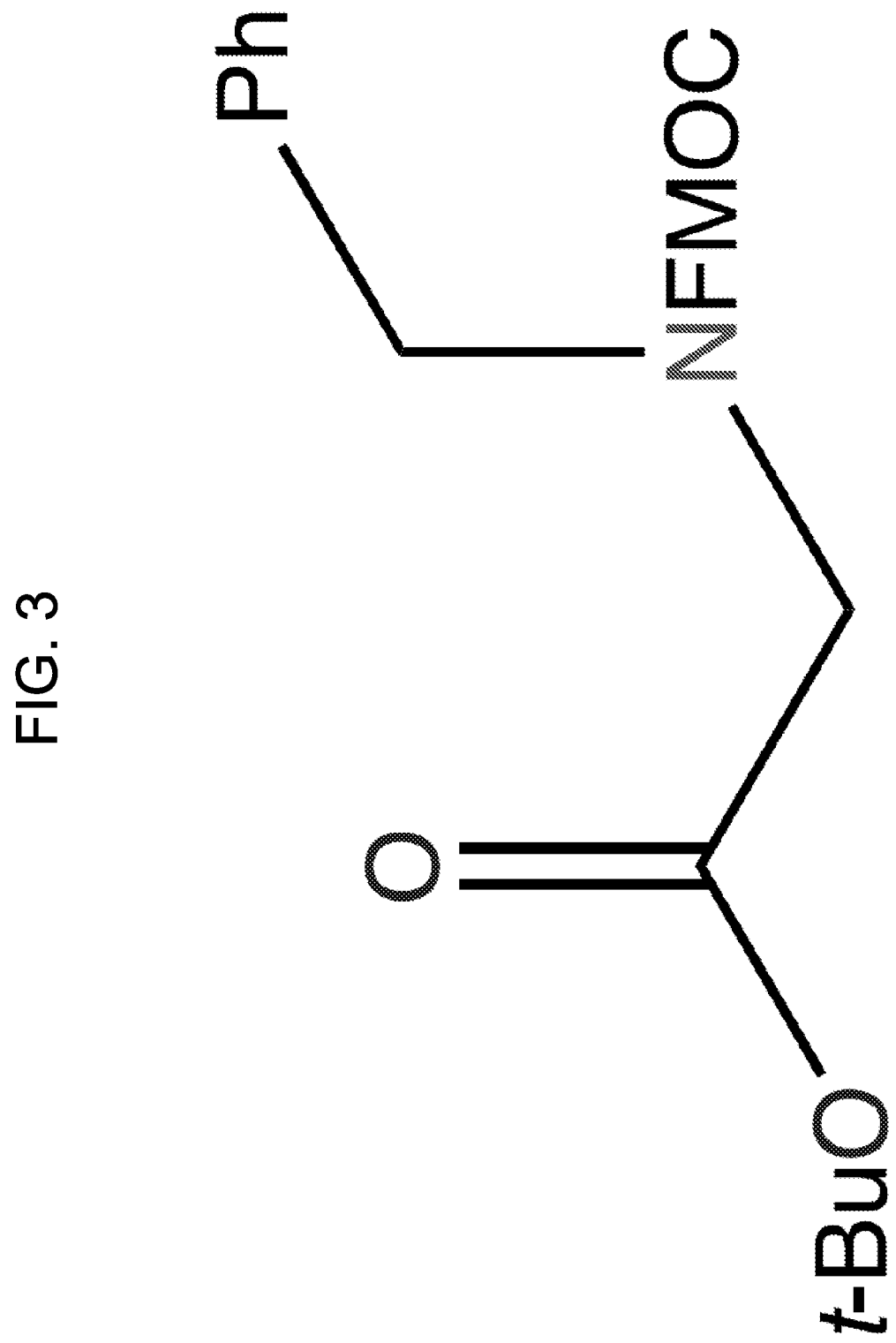
FIG. 3 shows a chemical structure of the example peptoid monomer of FIG. 2 altered to substitute a FMOC protective group for a hydrogen, in accordance with embodiments of the present disclosure.

FIG. 3 illustrates the peptoid monomer t-BuO₂CCH₂NFMOC(CH₂PH) synthesized from t-BuO₂CCH₂NHCH₂Ph. One skilled in the art will appreciate that t-BuO₂CCH₂NFMOC(CH₂Ph) is merely an illustrative peptoid monomer, and that other peptoid monomers may be synthesized in accordance with the present disclosure.

9-fluorenylmethyl chloroformate (FMOC-Cl) (about 17.2 g, about 67 mmol, 1.0 eq.) was added, in small portions, to a solution of BuO₂CCH₂NHCH₂Ph (about 17.6 g, about 80 mmol, 1.2 eq.) in dichloromethane (CH₂Cl₂) (about 250 mL) contained in a RBF (e.g., a 500 mL RBF). CH₂Cl₂, (about 70 mL) was used to complete the transfer of FMOC-Cl, resulting in an about 0.25 M initial concentration of FMOC-Cl. After stirring for about 4.5 hrs under Ar, the solution was extracted with about 0.1 M aqueous hydrochloric acid (HCl) (about 500 mL, 2×250 mL) and brine (about 250 mL). The resulting organic phase was dried over Na₂SO₄, filtered, and concentrated to an oil. The resulting oil was dissolved in minimal EtOAc, and a seed crystal was added. The resulting solution was allowed to crystallize at about 4° C. overnight. The resulting slurry was filtered, washed with minimal EtOAc, and dried under high vacuum. The filtrate was evaporated and treated in the same manner twice to obtain two more crops of product, about 2.26 g and about 2.33 g respectively, resulting in about 20.2 g t-BuO₂CCH₂NFMOC(CH₂PH) (about 57% yield).

HO₂CCH₂NFMOC(CH₂Ph)

Figure 4:
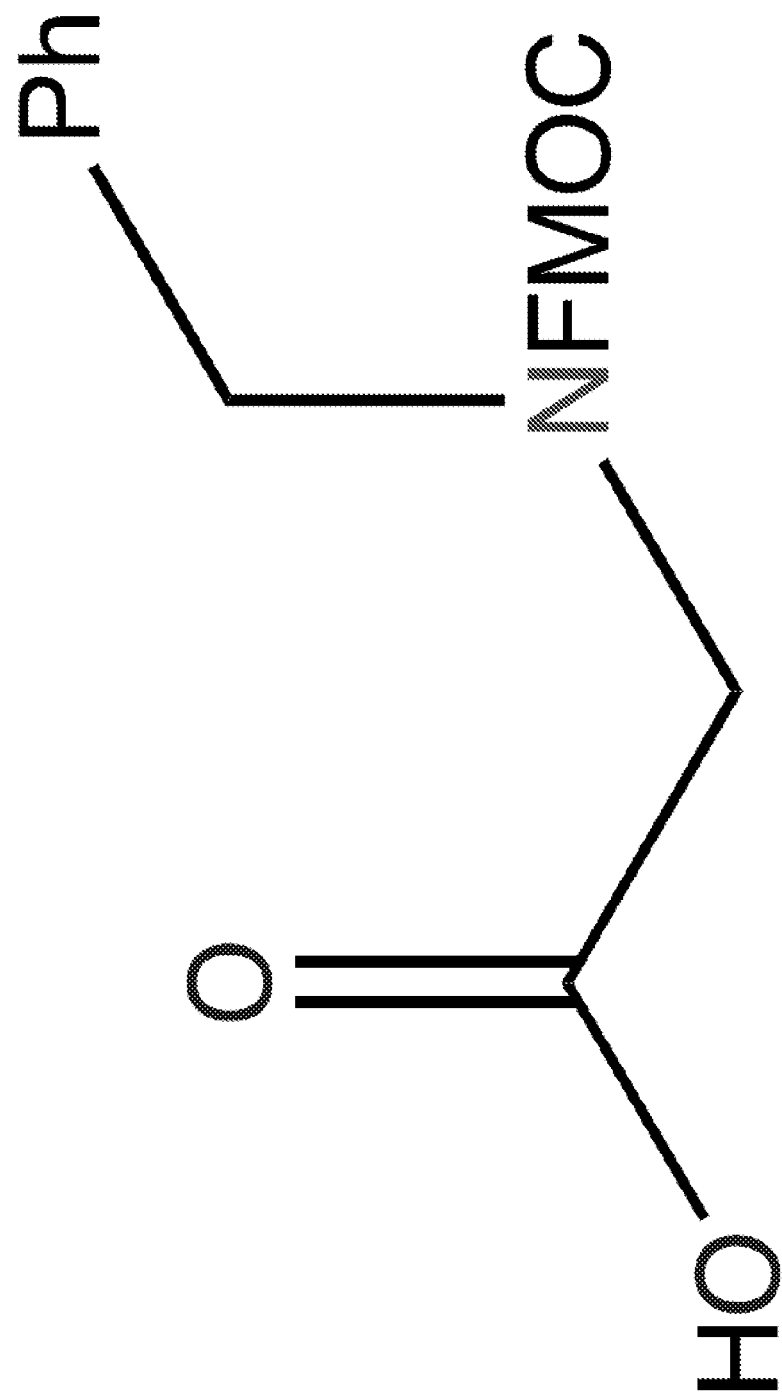
FIG. 4 shows a chemical structure of the example peptoid monomer of FIG. 3 altered to substitute a hydrogen for a t-butyl protective group, in accordance with embodiments of the present disclosure.

FIG. 4 illustrates the peptoid monomer HO₂CCH₂NFMOC(CH₂Ph) synthesized from t-BuO₂CCH₂NFMOC(CH₂PH). One skilled in the art will appreciate that HO₂CCH₂NFMOC(CH₂Ph) is merely an illustrative peptoid monomer, and that other peptoid monomers may be synthesized in accordance with the present disclosure.

t-BuO₂CCH₂NFMOC(CH₂PH) (about 15 g, about 34 mmol, 1.0 eq.) was added to a RBF (e.g., a 1 L RBF), followed by addition of triisopropylsilane (i-Pr₃SiH) (about 21 mL, about 102 mmol, 3.0 eq.). Trifluoroacetic acid (TFA) (about 68 mL, about 0.5 M) was added to the resulting slurry, followed by addition of CH₂Cl₂ (about 5 mL). The resulting mixture was stirred at rt for about 1.5 hrs, then evaporated under vacuum and evaporated with toluene (about 150 mL, 3×50 mL). The resulting crude product was dried under high vacuum overnight. The resulting solid was triturated with hexanes (about 100 mL), washed with hexanes (about 100 mL, 2×50 mL), and dried under high vacuum, resulting in about 12.9 g HO₂CCH₂NFMOC (CH₂Ph) (about 99% yield).

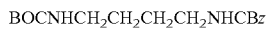
BOCNHCH₂CH₂CH₂CH₂NHCBz

Figure 5:
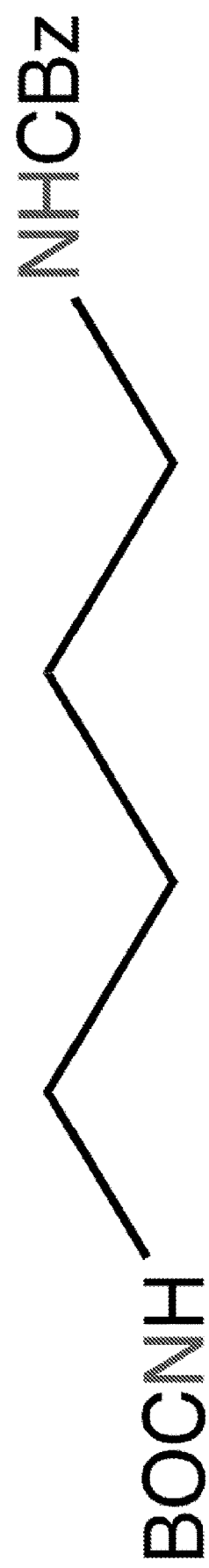
FIG. 5 shows a chemical structure of an example side chain, in accordance with embodiments of the present disclosure.

FIG. 5 illustrates the side chain, BOCNHCH₂CH₂CH₂CH₂NHCBz. One skilled in the art will appreciate that BOCNHCH₂CH₂CH₂CH₂NHCBz is merely an illustrative side chain, and that other side chains may be synthesized in accordance with the present disclosure.

Triethylamine (about 16 mL, about 116 mmol, 2.5 eq.) was added to a stirring slurry of BOCNHCH₂CH₂CH₂CH₂NH₃Cl (about 10.4 g, about 46 mmol, 1.0 eq.) in tetrahydrofuran (THF) (about 92 mL, about 0.5 M), contained in a RBF (e.g., a 250 mL RBF). The resulting slurry was chilled in an ice bath and N-(benzyloxycarbonyloxy)succinimide (CBz-OSu) (about 11.5 g, about 46 mmol, 1.0 eq.) was then added in portions. The reaction mixture was then stirred under Ar at about 0° C. for about 5 minutes, warmed to rt, then stirred at rt overnight. The solvent was then removed from the reaction mixture via rotary evaporation. H₂O (about 100 mL) was added and the mixture was extracted with EtOAc (about 1502 mL, 3×50 mL), washed with aqueous 0.1 M HCl (about 100 mL) and brine (about 100 mL), and dried over Na₂SO₄. The solution was filtered and concentrated to dryness yielding a white colored solid produce (BOCNHCH₂CH₂CH₂CH₂NHCBz). The product was spectroscopically pure after drying overnight under high vacuum. The product weighed about 14.2 g (about 95% yield).

CBzNHCH₂CH₂CH₂CH₂NH₃Cl

Figure 6:
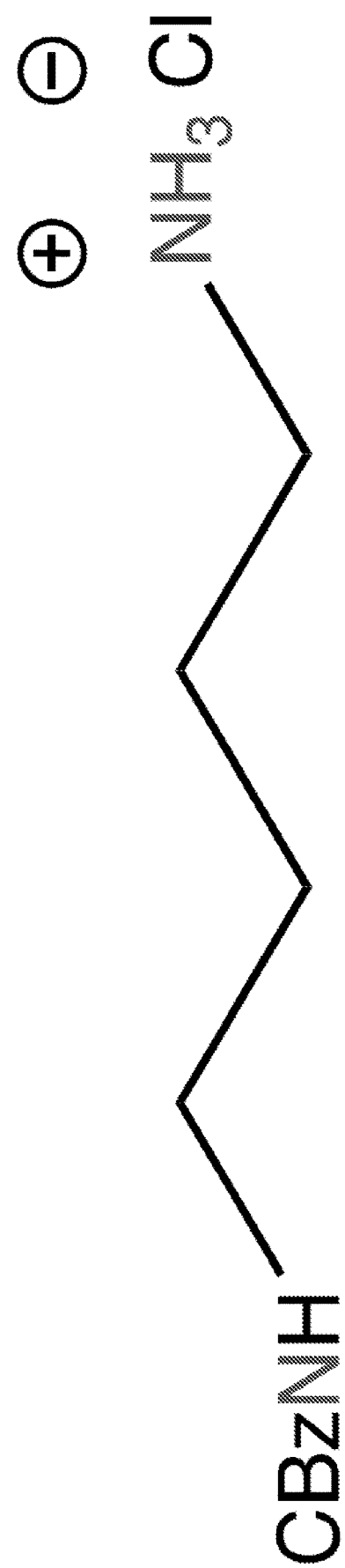
FIG. 6 shows a chemical structure of the example side chain of FIG. 5 altered to substitute a BOC protective group with CBz, in accordance with embodiments of the present disclosure.

FIG. 6 illustrates the side chain CBzNHCH₂CH₂CH₂CH₂NH₃Cl synthesized from BOCNHCH₂CH₂CH₂CH₂NHCBz. One skilled in the art will appreciate that CBzNHCH₂CH₂CH₂CH₂NH₃Cl is merely an illustrative side chain, and that other side chains may be synthesized in accordance with the present disclosure.

BOCNHCH₂CH₂CH₂CH₂NHCBz (about 14.2 g, about 44 mmol, 1.0 eq.) was added to a RBF (e.g., a 500 mL RBF), followed by addition of 1,4-dioxane (about 90 mL). To the resulting solution, 4M HCl-Dioxane (about 55 mL, about 220 mmol, 5.0 eq.) was added (e.g., via syringe). The resulting mixture was stirred under Ar overnight, resulting in the precipitation of a white colored solid. The resulting mixture was filtered and the solid was washed with THF (about 100 mL, 2×50 mL) and dried under high vacuum, yielding about 10.9 g of a white colored powder (about 95% yield).

t-BuO₂CCH₂NH(C₄H₈NHCBz)

Figure 7:
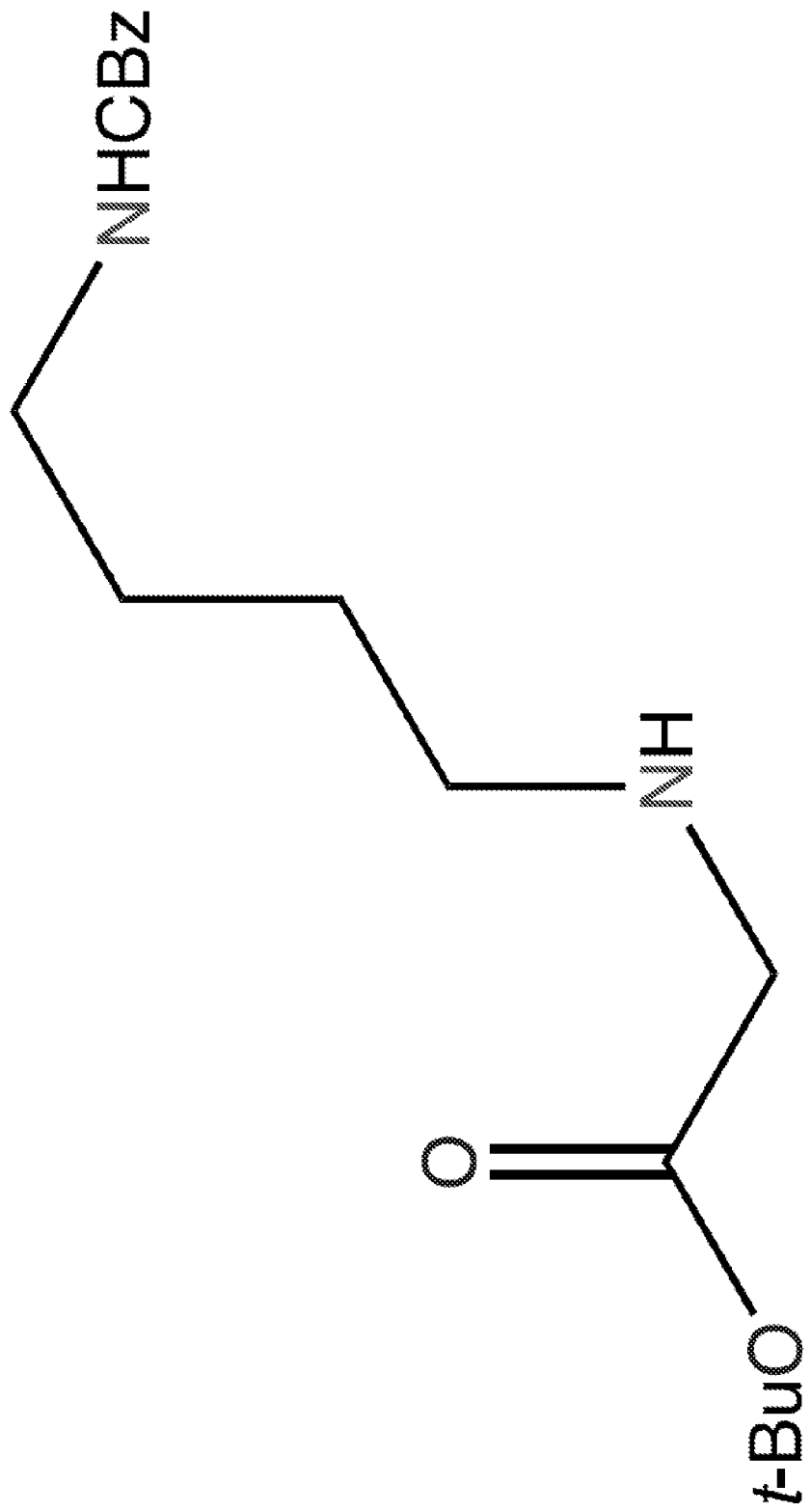
FIG. 7 shows a chemical structure of the example side chain of FIG. 6 appended to a peptoid monomer and altered to substitute an amine with a CBz protective group, in accordance with embodiments of the present disclosure.

FIG. 7 illustrates the peptoid monomer t-BuO$_2$CCH$_2$NH(C$_4$H$_8$NHCBz) synthesized from CBzNHCH$_2$CH$_2$CH$_2$CH$_2$NH$_3$Cl. One skilled in the art will appreciate that t-BuO$_2$CCH$_2$NH(C$_4$H$_8$NHCBz) is merely an illustrative peptoid monomer, and that other peptoid monomers may be synthesized in accordance with the present disclosure.

Triethylamine (about 12.3 mL, about 88 mmol, 2.0 eq.) was added to a stirring solution of CBzNHCH$_2$CH$_2$CH$_2$CH$_2$NH$_3$Cl (about 11.4 g, about 44 mmol, 1.0 eq.) in DMF (about 70 mL) contained in a RBF (e.g., a 250 mL RBF) at about 0° C. The reaction mixture was stirred for about 5 minutes and a solution of tert-butylbromoacetate (t-BuO$_2$CCH$_2$Br) (about 5.9 mL, about 40 mmol, 0.9 eq.) in DMF (about 18 mL) was added dropwise (e.g., from an addition funnel), achieving an initial concentration of t-BuO$_2$CCH$_2$Br of about 0.5 M. After the addition was complete (after about 0.5 hours), the reaction mixture was allowed to warm to rt. After stirring overnight, the reaction mixture was diluted with H$_2$O (about 250 mL), extracted with EtOAc (about 100 mL, 2×50 mL). The organic phase was then washed with brine (about 100 mL, 2×50 mL), dried over Na$_2$SO$_4$, filtered, and concentrated to an oil. The crude product was purified via flash chromatography on silica with a gradient of EtOAc/hexanes, yielding about 9.0 g of an oil product (about 67% yield).

*t*-BuO$_2$CCH$_2$NFMOC(C$_4$H$_8$NHCB*z*)

Figure 8:
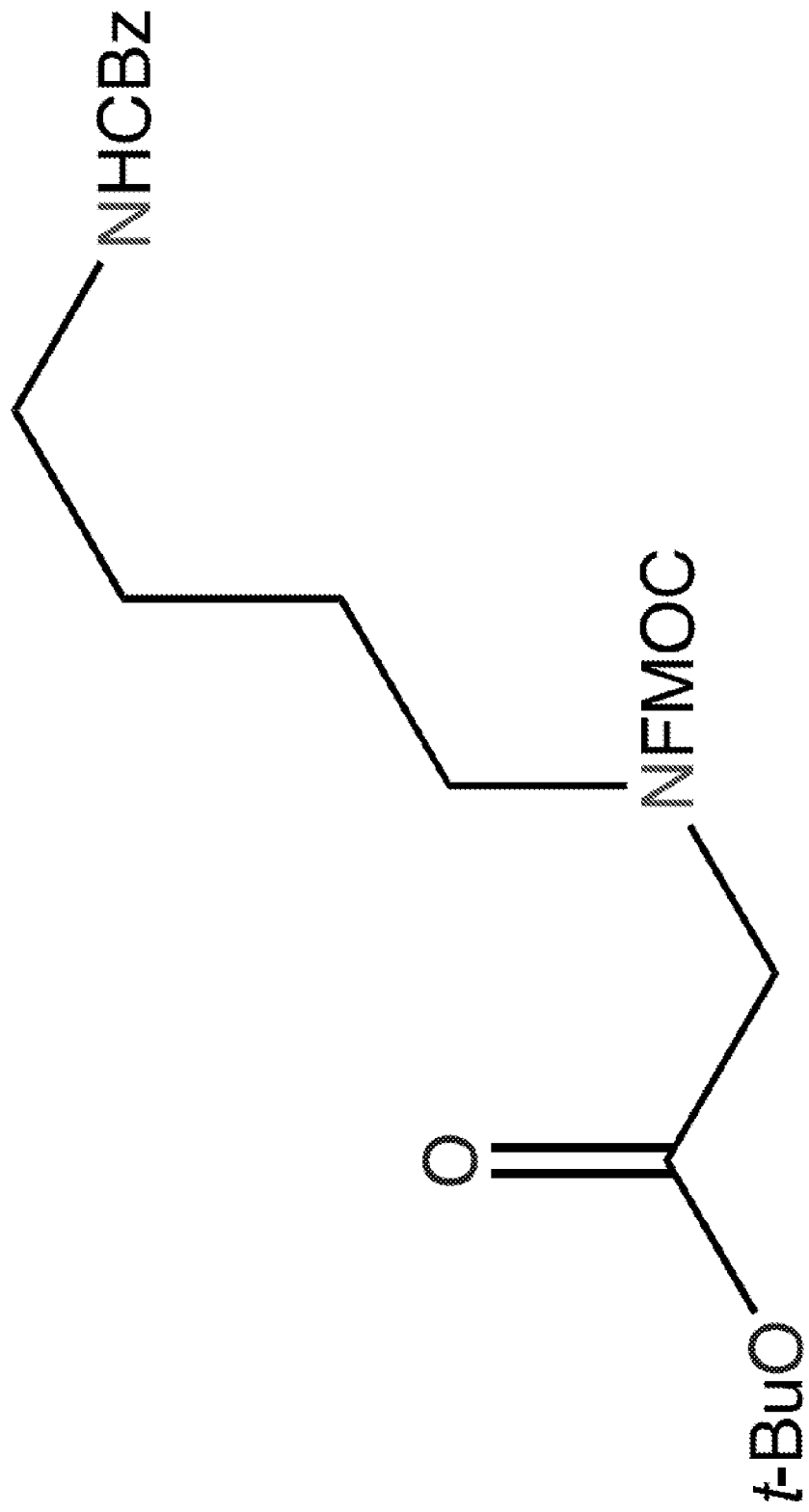
FIG. 8 is a chemical structure of the example peptoid monomer of FIG. 7 altered to substitute a hydrogen with a FMOC protective group, in accordance with embodiments of the present disclosure.

FIG. 8 illustrates the peptoid monomer t-BuO$_2$CCH$_2$NFMOC(C$_4$H$_8$NHCBz) synthesized from t-BuO$_2$CCH$_2$NH(C$_4$H$_8$NHCBz). One skilled in the art will appreciate that t-BuO$_2$CCH$_2$NFMOC(C$_4$H$_8$NHCBz) is merely an illustrative peptoid monomer, and that other peptoid monomers may be synthesized in accordance with the present disclosure.

FMOC-Cl (about 4.3 g, about 16.8 mmol, 1.0 eq.) was added, in small portions, to a stirring solution of t-BuO$_2$CCH$_2$NH(C$_4$H$_8$NHCBz) (about 6.8 g, about 20.2 mmol, 1.2 eq.) in 0.25M CH$_2$Cl$_2$ (about 68 mL). The reaction mixture was then stirred overnight at rt. The resulting solution was then diluted with aqueous 0.1 M HCl (about 100 mL) and the aqueous layer extracted with CH$_2$Cl$_2$ (about 50 mL, 2×25 mL). The combined organic phase was washed with brine (about 50 mL), dried over Na$_2$SO$_4$, filtered, and concentrated to dryness. The resulting oil was dissolved in methanol (MeOH) and chilled in a freezer overnight, resulting in the product crystallizing. The product was filtered and washed with a small amount of MeOH. Thin-layer chromatograph (TLC) indicated non-polar FMOC containing by-products. The resulting solid was stirred with hexanes (about 25 mL), filtered, and washed with hexanes (about 50 mL, 2×25 mL). The resulting solid was dried under high vacuum. A second crop of crystals was obtained in the same manner from the initial filtrate, producing about 6.4 g (about a 68% combined yield).

HO$_2$CCH$_2$NFMOC(C$_4$H$_8$NHCB*z*)

Figure 9:
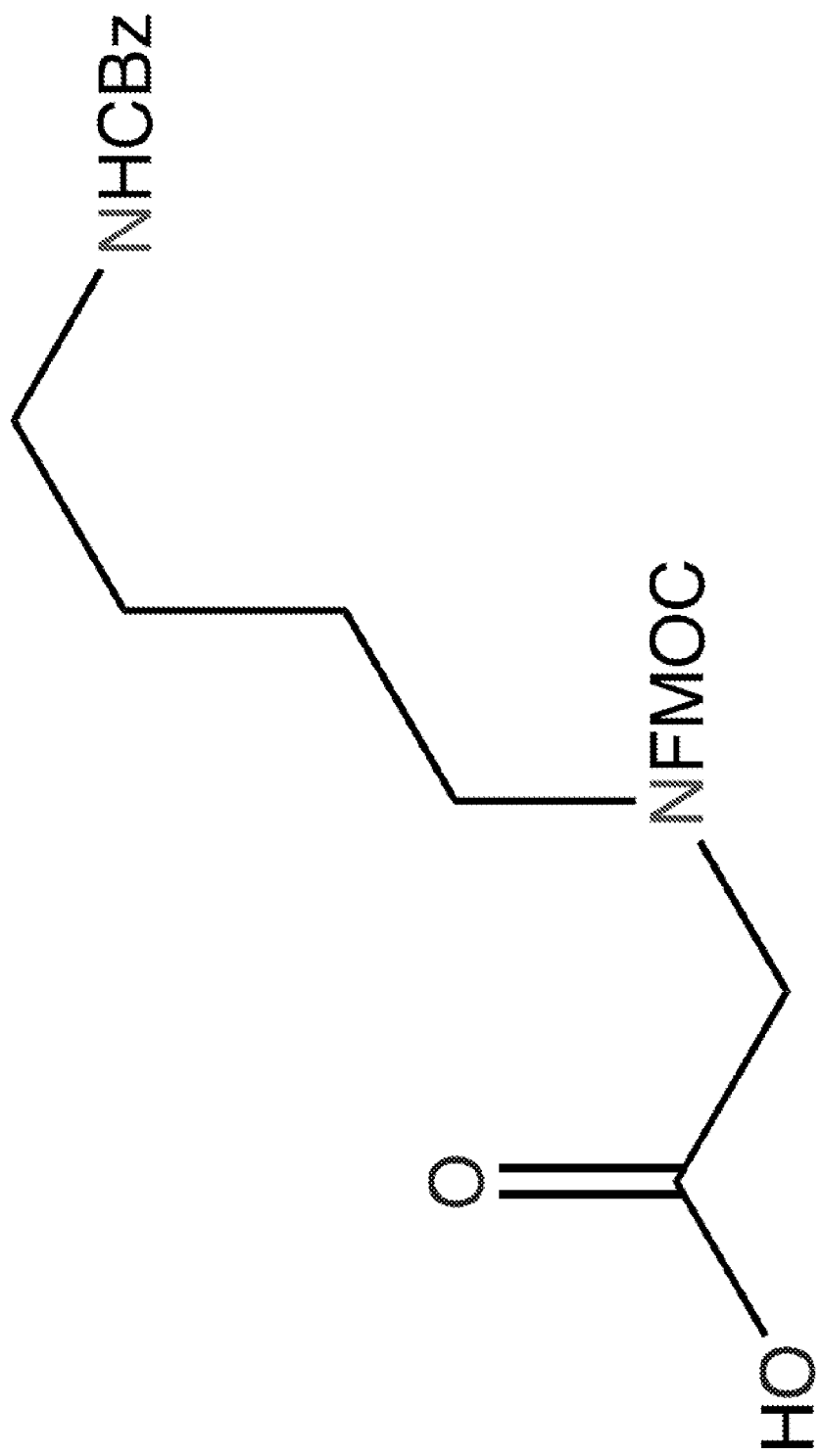
FIG. 9 is a chemical structure of the example peptoid monomer of FIG. 8 altered to substitute a t-Bu protective group with a hydrogen, in accordance with embodiments of the present disclosure.

FIG. 9 illustrates the peptoid monomer HO$_2$CCH$_2$NFMOC(C$_4$H$_8$NHCBz) synthesized from t-BuO$_2$CCH$_2$NFMOC(C$_4$H$_8$NHCBz). One skilled in the art will appreciate that HO$_2$CCH$_2$NFMOC(C$_4$H$_8$NHCBz) is merely an illustrative peptoid monomer, and that other peptoid monomers may be synthesized in accordance with the present disclosure.

i-Pr$_3$SiH, (about 11.7 mL, about 57.3 mmol, 5.0 eq.) was added to a RBF (e.g., a 500 mL RBF) containing t-BuO$_2$CCH$_2$NFMOC(C$_4$H$_8$NHCBz) (about 6.4 g, about 11.5 mmol, 1.0 eq.), resulting in the formation of a slurry. TFA (about 58 mL, about 0.2M) was then added slowly. The resulting mixture was stirred at rt for about 1 hr, after which time TLC indicated complete consumption of starting material. Volatiles were then removed with a rotary evaporator, leaving an oil that was evaporated with toluene (about 75 mL, 3×25 mL), and then dried under high vacuum for about 4 hrs. The resulting oil was triturated with hexanes (about 100 mL), the solvent decanted, and the resultant material dissolved in minimal EtOAc. Hexane was slowly added until the solution turned cloudy. This was then heated in an about 40° C. water bath until the solution cleared. A seed crystal was added, and the mixture was allowed to crystallize overnight at rt. The resulting solid was filtered and washed with 50% EtOAc/hexanes (about 70 mL, 2×35 mL), and then dried under high vacuum, to yield about 4.1 g (about 70% yield) of HO$_2$CCH$_2$NFMOC(C$_4$H$_8$NHCBz) as a white colored powder.

*t*-BuO$_2$CCH$_2$N(B*n*)COCH$_2$NFMOC(C$_4$H$_8$NHCB*z*)

Figure 10:
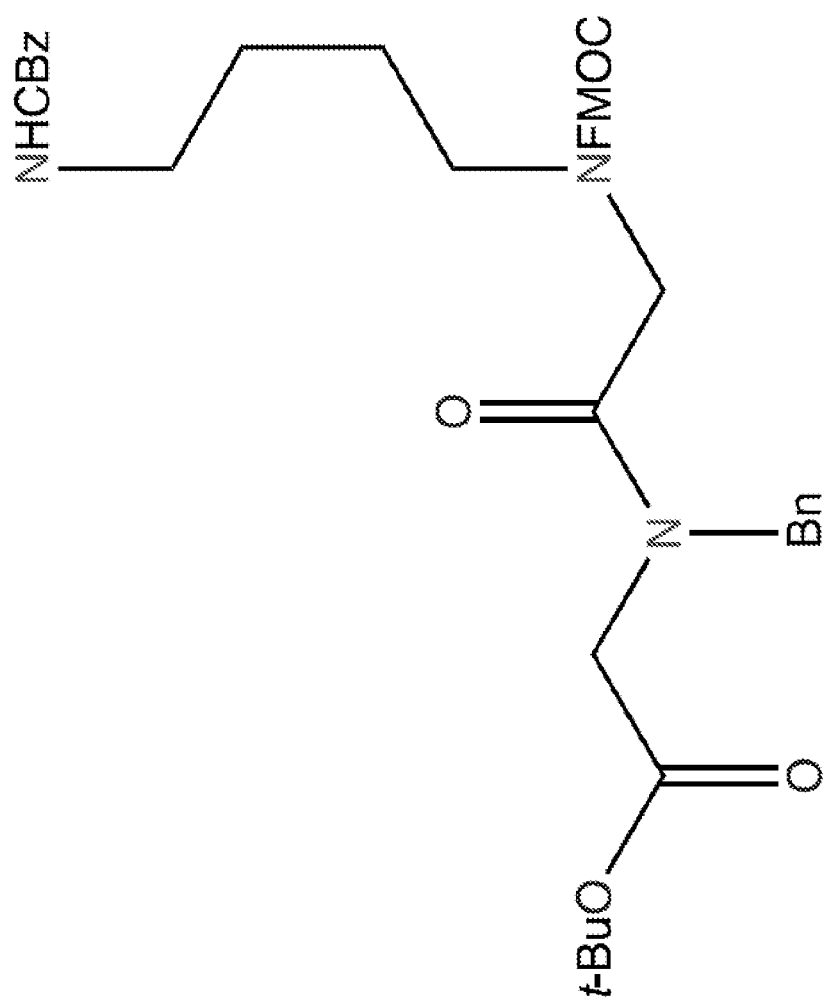
FIG. 10 is a chemical structure of the example peptoid monomer of FIG. 9 altered to substitute a hydroxyl group with a second peptoid monomer t-BuO$_2$CCH$_2$N(Bn), in accordance with embodiments of the present disclosure.

FIG. 10 illustrates the peptoid t-BuO$_2$CCH$_2$N(Bn)COCH$_2$NFMOC(C$_4$H$_8$NHCBz) synthesized from HO$_2$CCH$_2$NFMOC(C$_4$H$_8$NHCBz). One skilled in the art will appreciate that t-BuO$_2$CCH$_2$N(Bn)COCH$_2$NFMOC(C$_4$H$_8$NHCBz) is merely an illustrative peptoid, and that other peptoids may be synthesized in accordance with the present disclosure.

Ethyl (hydroxyamino) cyanoacetate (oxyma) (about 0.85 g, about 6.0 mmol, 1.0 eq.) was added to a solution of HO$_2$CCH$_2$NFMOC(C$_4$H$_8$NHCBz) (about 3.0 g, about 6.0 mmol, 1.0 eq.) in DMF (about 20 mL). After stirring for about 5 minutes, N,N-diisopropylcarbodiimide (DIC) (about 0.93 mL, 1.0 eq.) was added. After stirring for an additional about 5 minutes, t-BuO$_2$CCH$_2$NHBn (about 1.32 g, about 6.0 mmol, 1.0 eq.) was added in DMF (about 10 mL) and the reaction mixture was stirred overnight at rt. The reaction mixture was then diluted with H$_2$O (about 100 mL), and extracted with EtOAc (about 75 mL, 1×50 mL, 2×25 mL). The organic phase was then washed with H$_2$O (about 50 mL, 2×25 mL), saturated aqueous NaHCO$_3$ (about 75 mL, 3×25 mL), and brine (about 50 mL). The organic phase was then dried over Na$_2$SO$_4$, filtered, and concentrated to yield an oil. The product was purified by flash chromatography on silica using EtOAc/hexanes, yielding about 3.9 g of a white colored foam after drying under high vacuum (about 92% yield).

HO$_2$CCH$_2$N(B*n*)COCH$_2$NFMOC(C$_4$H$_8$NHCB*z*)

Figure 11:
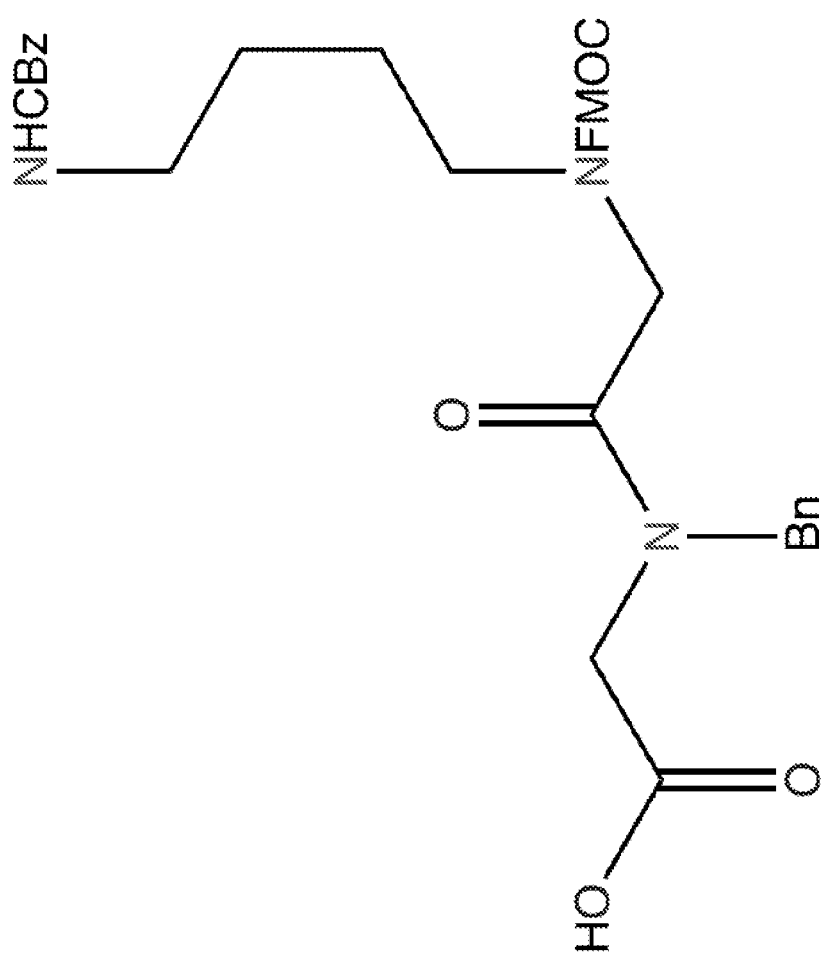
FIG. 11 is a chemical structure of the example peptoid of FIG. 10 altered to substitute a t-Bu protective group with a hydrogen, in accordance with embodiments of the present disclosure.

FIG. 11 illustrates the peptoid HO$_2$CCH$_2$N(Bn)COCH$_2$NFMOC(C$_4$H$_8$NHCBz) synthesized from the peptoid t-BuO$_2$CCH$_2$N(Bn)COCH$_2$NFMOC(C$_4$H$_8$NHCBz). One skilled in the art will appreciate that HO$_2$CCH$_2$N(Bn)COCH$_2$NFMOC(C$_4$H$_8$NHCBz) is merely an illustrative peptoid, and that other peptoids may be synthesized in accordance with the present disclosure.

i-Pr$_3$SiH (about 1.45 mL, about 7.1 mmol, 5.0 eq.) was added to a RBF (e.g., a 50 mL RBF) containing t-BuO$_2$CCH$_2$N(Bn)COCH$_2$NFMOC(C$_4$H$_8$NHCBz) (about 1.0 g, about 1.4 mmol, 1.0 eq.), followed by addition of TFA (about 5.8 mL, about 0.25 M). CH$_2$Cl$_2$ (about 1.0 mL) was then added. The resulting mixture was stirred at rt for about 35 min, after which time TLC indicated consumption of starting material. The resulting solution was evaporated to an oil and evaporated with CH$_2$Cl$_2$ (about 30 mL, 3×10 mL). The crude product was loaded onto silica gel from CH$_2$Cl$_2$ and purified via flash chromatography on silica using a gradient of EtOAc/hexanes. About 0.82 g of the product was obtained as a white colored foam after evaporation of the product containing fractions (about 89% yield).

t-BuO$_2$CCH$_2$N(C$_4$H$_8$NHCBz)COCH$_2$N(B$n$)
COCH$_2$NFMOC(C$_4$H$_8$NHCBz)

Figure 12:
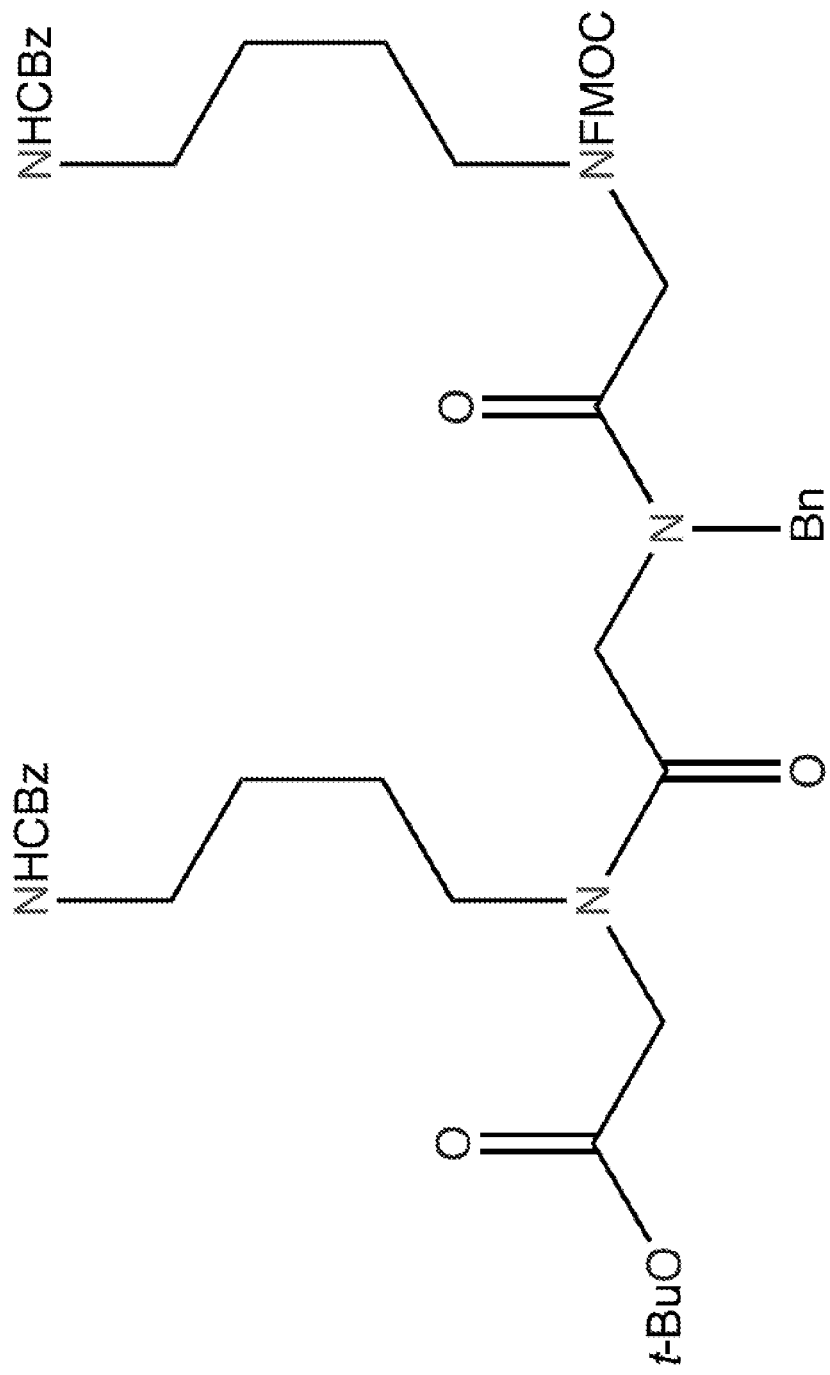
FIG. 12 is a chemical structure of the example peptoid of FIG. 11 altered to substitute a hydrogen with the peptoid t-BuO$_2$CCH$_2$N(C$_4$H$_8$NHCBz), in accordance with embodiments of the present disclosure.

FIG. 12 illustrates the peptoid t-BuO$_2$CCH$_2$N(C$_4$H$_8$NHCBz)COCH$_2$N(Bn)COCH$_2$NFMOC(C$_4$H$_8$NHCBz) synthesized from the peptoid HO$_2$CCH$_2$N(Bn)COCH$_2$NFMOC(C$_4$H$_8$NHCBz). One skilled in the art will appreciate that t-BuO$_2$CCH$_2$N(C$_4$H$_8$NHCBz)COCH$_2$N(Bn)COCH$_2$NFMOC(C$_4$H$_8$NHCBz) is merely an illustrative peptoid, and that other peptoids may be synthesized in accordance with the present disclosure.

Bromotripyrrolidinophosphonium hexafluorphosphate (PyBrOP) (about 0.58 g, 1.2 eq.) was added to a solution of HO$_2$CCH$_2$N(Bn)COCH$_2$NFMOC(C$_4$H$_8$NHCBz) (about 0.73 g, about 1.1 mmol, 1.0 eq.) in CH$_2$Cl$_2$ (about 6 mL), followed by addition of N,N-diisopropylethylamine (i-Pr$_2$NEt) (about 0.39 mL, about 2.2 mmol, 2.0 eq.). The resulting solution was stirred for about 5 min and a solution of t-BuO$_2$CCH$_2$NH(C$_4$H$_8$NHCBz) (about 0.38 g, about 1.1 mmol, 1.0 eq.) in CH$_2$Cl$_2$ (about 6 mL) was added. Limiting reagent concentration was about 0.1 M. The reaction mixture was stirred overnight and poured into a saturated aqueous NaHCO$_3$ solution (about 100 mL). The mixture was extracted with EtOAc (about 100 mL, 1×75 mL, 1×25 mL) and the organic phase was washed with brine (about 50 mL). The resulting solution was dried over Na$_2$SO$_4$, filtered, and concentrated to an oil. The oil was dissolved in CH$_2$Cl$_2$, loaded onto silica, and purified via flash chromatography on silica using EtOAc/hexanes, resulting in about 0.76 g of product (about 70% yield).

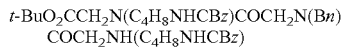
t-BuO$_2$CCH$_2$N(C$_4$H$_8$NHCBz)COCH$_2$N(B$n$)
COCH$_2$NH(C$_4$H$_8$NHCBz)

Figure 13:
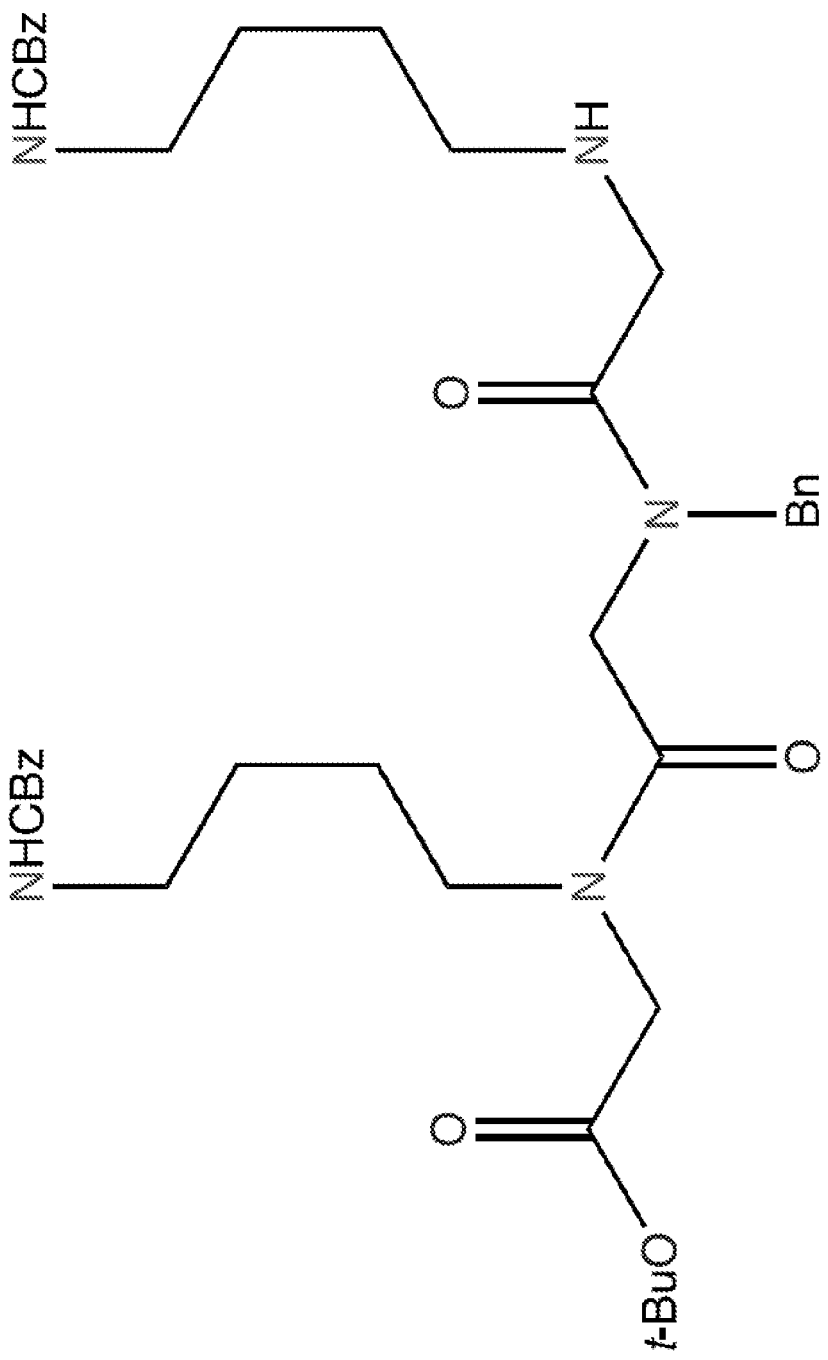
FIG. 13 is a chemical structure of the example peptoid of FIG. 12 altered to substitute a FMOC protective group with a hydrogen, in accordance with embodiments of the present disclosure.

FIG. 13 illustrates the peptoid t-BuO$_2$CCH$_2$N(C$_4$H$_8$NHCBz)COCH$_2$N(Bn)COCH$_2$NH(C$_4$H$_8$NHCBz) synthesized from the peptoid t-BuO$_2$CCH$_2$N(C$_4$H$_8$NHCBz)COCH$_2$N(Bn)COCH$_2$NFMOC(C$_4$H$_8$NHCBz). One skilled in the art will appreciate that t-BuO$_2$CCH$_2$N(C$_4$H$_8$NHCBz)COCH$_2$N(Bn)COCH$_2$NH(C$_4$H$_8$NHCBz) is merely an illustrative peptoid, and that other peptoids may be synthesized in accordance with the present disclosure.

20% piperidine in tetrahydrofuran (THF) (about 22 mL, about 0.1 M) was added to a RBF (e.g., a 250 mL RBF) containing t-BuO$_2$CCH$_2$N(C$_4$H$_8$NHCBz)COCH$_2$N(Bn)COCH$_2$NFMOC(C$_4$H$_8$NHCBz) (about 2.2 g, about 2.2 mmol, 1.0 eq.). The walls of the RBF were washed down with THF. The mixture was stirred vigorously and, after about 20 minutes, TLC indicated complete consumption of starting material. The resulting mixture was evaporated to dryness and evaporated with several small portions of toluene to remove excess piperidine. The resulting product was loaded onto silica gel using CH$_2$Cl$_2$ and evaporated, and purified via flash chromatography on silica using a gradient of EtOAc/hexanes, then switching to a gradient of MeOH/EtOAc. The resulting product containing fractions were collected, concentrated, and dried under high vacuum, yielding about 1.62 g of the product as a white colored foam (about 98% yield).

t-BuO$_2$CCH$_2$N(C$_4$H$_8$NHCBz)COCH$_2$NFMOC(B$n$)

Figure 14:
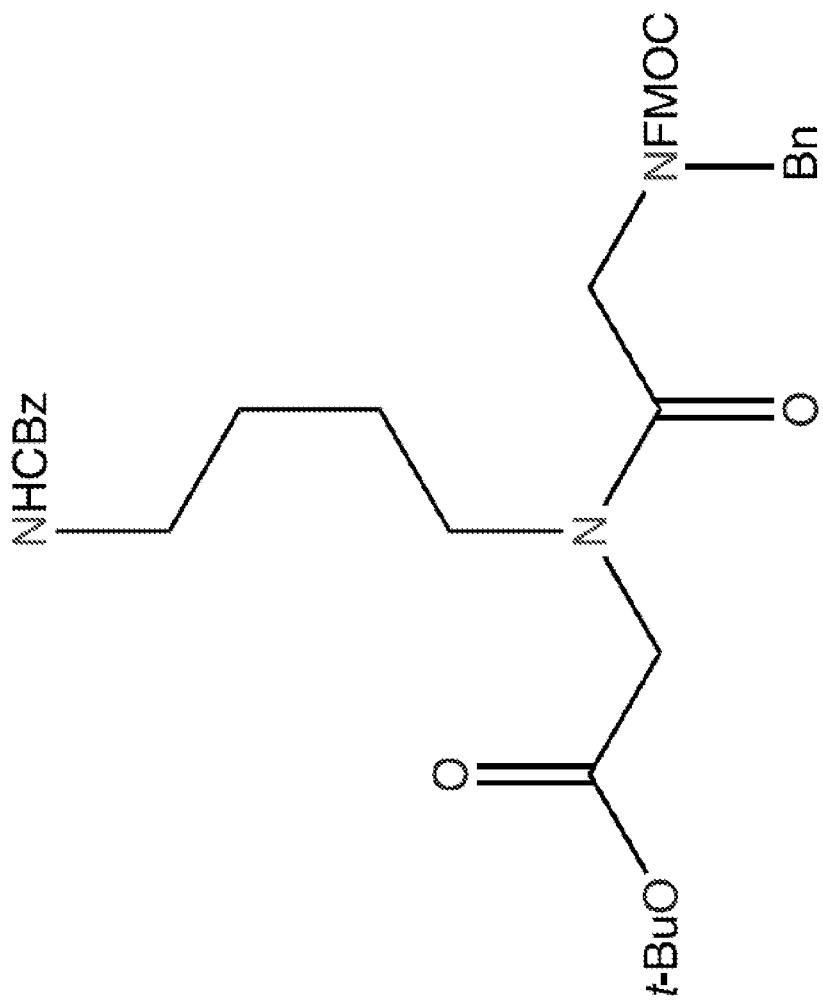
FIG. 14 is a chemical structure of the example peptoid monomer of FIG. 4 altered to substitute a hydrogen with a second peptoid t-BuO$_2$CCH$_2$N(C$_4$H$_8$NHCBz), in accordance with embodiments of the present disclosure.

FIG. 14 illustrates the peptoid t-BuO$_2$CCH$_2$N(C$_4$H$_8$NHCBz)COCH$_2$NFMOC(Bn) synthesized from HO$_2$CCH$_2$NFMOC(Bn). One skilled in the art will appreciate that t-BuO$_2$CCH$_2$N(C$_4$H$_8$NHCBz)COCH$_2$NFMOC(Bn) is merely an illustrative peptoid, and that other peptoids may be synthesized in accordance with the present disclosure.

Oxyma (about 1.1 g, about 7.7 mmol, 1.0 eq.) was added to a solution of HO$_2$CCH$_2$NFMOC(Bn) (about 3.0 g, about 7.7 mmol, 1.0 eq.) in DMF (about 30 mL) contained in a RBF (e.g., a 100 mL RBF). The resulting solution was stirred for about 5 minutes. DIC (about 1.2 mL, about 7.7 mmol, 1.0 eq.) was added to the reaction mixture, which was then stirred for about 10 minutes. A solution of t-BuO$_2$CCH$_2$NH(C$_4$H$_8$NHCBz) (about 2.6 g, about 7.7 mmol, 1.0 eq.) in DMF (about 9.0 mL) was then added, achieving an initial limiting reactant concentration of about 0.2 M. The reaction mixture was stirred overnight and subsequently diluted with H$_2$O (about 100 mL). The mixture was then extracted with EtOAc (about 100 mL, 1×50 mL, 2×25 mL). The organic phase was then washed with H$_2$O (about 50 mL, 2×25 mL), and saturated with aqueous NaHCO$_3$ (about 75 mL, 3×25 mL) and brine (about 50 mL). The organic phase was then dried over Na$_2$SO$_4$, filtered, and concentrated. The resulting material was dissolved in CH$_2$Cl$_2$, loaded onto silica gel, and purified via flash chromatography on silica, using a gradient of EtOAc/hexanes to elute the product. Product containing fractions were concentrated and dried under high vacuum, yielding about 4.3 g of a white colored foam (about 80% yield).

HO$_2$CCH$_2$N(C$_4$H$_8$NHCBz)COCH$_2$NFMOC(B$n$)

Figure 15:
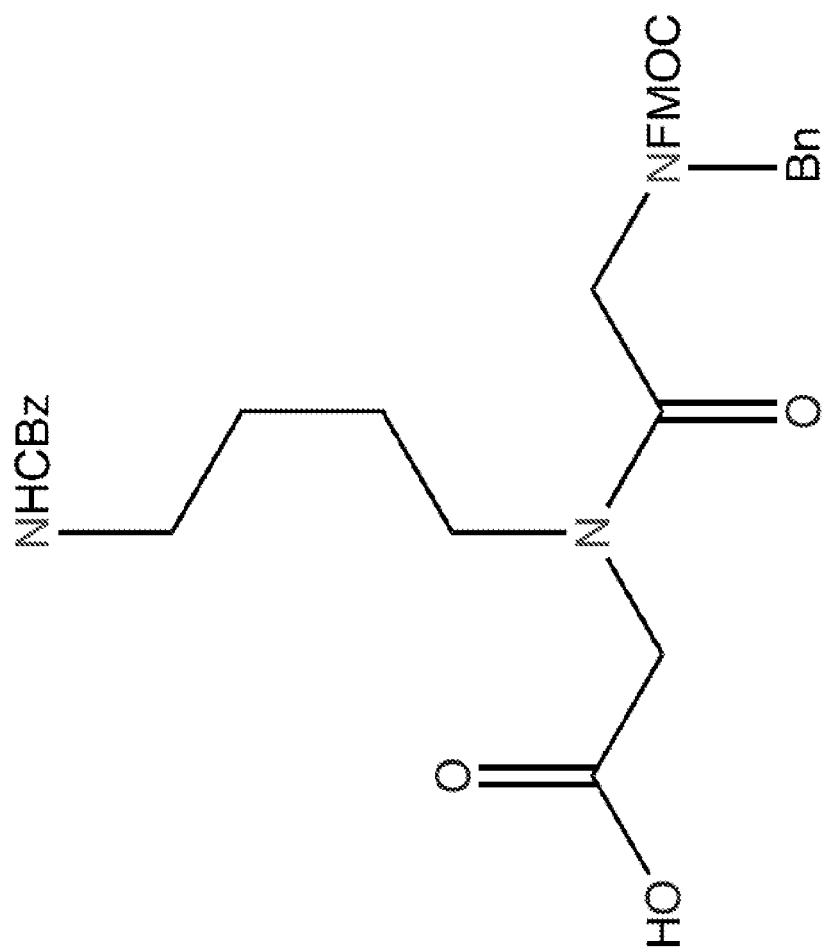
FIG. 15 is a chemical structure of the example peptoid of FIG. 14 altered to substitute t-Bu protective group with a hydrogen, in accordance with embodiments of the present disclosure.

FIG. 15 illustrates the peptoid HO$_2$CCH$_2$N(C$_4$H$_8$NHCBz)COCH$_2$NFMOC(Bn) synthesized from t-BuO$_2$CCH$_2$N(C$_4$H$_8$NHCBz)COCH$_2$NFMOC(Bn). One skilled in the art will appreciate that HO$_2$CCH$_2$N(C$_4$H$_8$NHCBz)COCH$_2$NFMOC(Bn) is merely an illustrative peptoid, and that other peptoids may be synthesized in accordance with the present disclosure.

i-Pr$_3$SiH (about 5.8 mL, about 28.3 mmol, 5.0 eq.) was added to a RBF (e.g., a 250 mL RBF) containing t-BuO$_2$CCH$_2$N(C$_4$H$_8$NHCBz)COCH$_2$NFMOC(Bn) (about 4.0 g, about 5.7 mmol, 1.0 eq.), followed by addition of TFA (about 23 mL, about 0.25 M) and CH$_2$Cl$_2$ (about 5.0 mL). The reaction mixture was stirred at rt, with complete disappearance of starting material observed via TLC after about 40 minutes. The reaction mixture was evaporated to dryness and evaporated with CH$_2$Cl$_2$ (about 20 mL, 2×10 mL). After drying under vacuum, the resulting oil was dissolved in CH$_2$Cl$_2$ and loaded onto silica gel. The product was then purified via flash chromatography on silica, eluting with a gradient of EtOAc/hexanes. The resulting product containing fractions were collected, concentrated, and dried under high vacuum, yielding about 3.0 g of a white colored foam (about 82% yield).

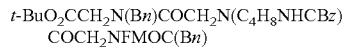
t-BuO$_2$CCH$_2$N(B$n$)COCH$_2$N(C$_4$H$_8$NHCBz)
COCH$_2$NFMOC(B$n$)

Figure 16:
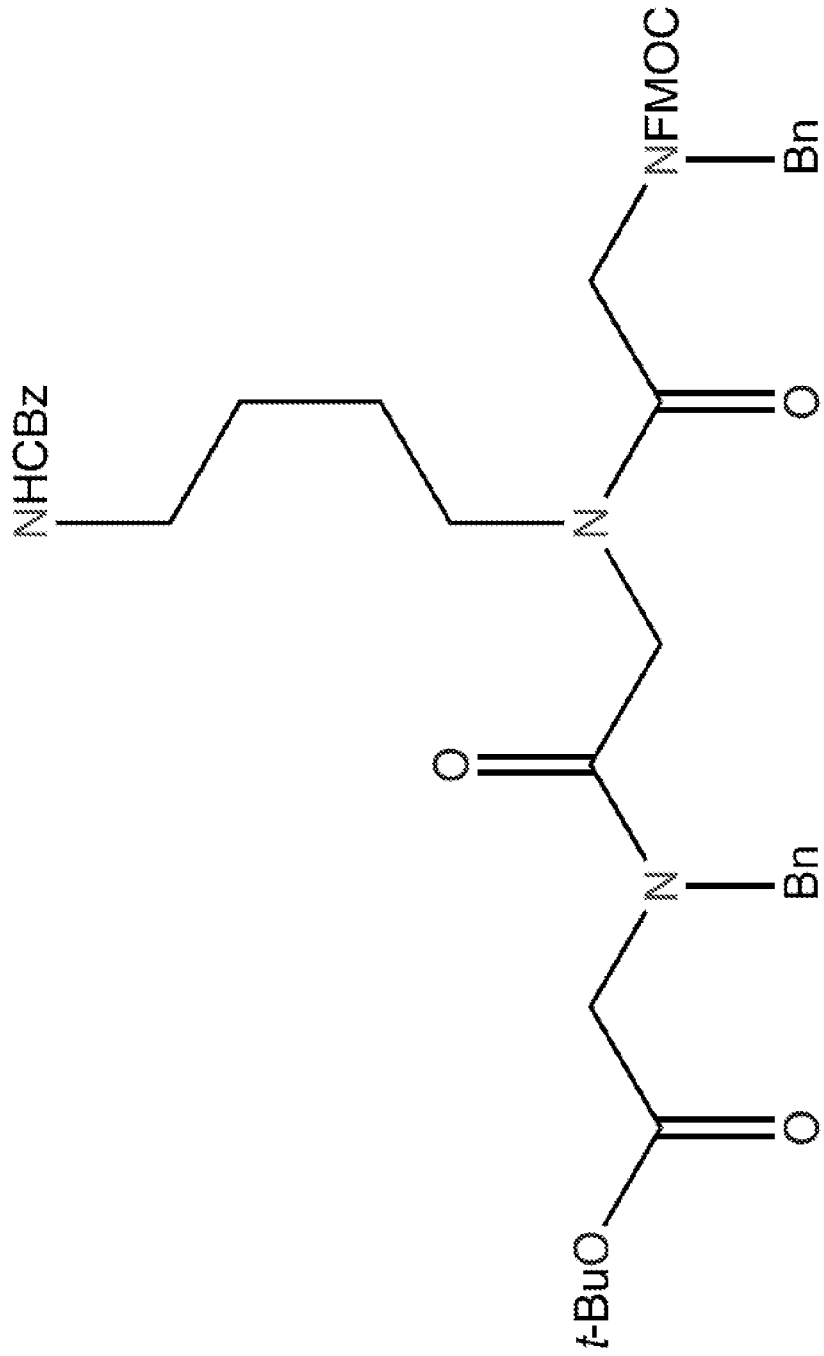
FIG. 16 is a chemical structure of the example peptoid of FIG. 15 altered to substitute a hydroxyl group with t-BuO$_2$CCH$_2$N(Bn), in accordance with embodiments of the present disclosure.

FIG. 16 illustrates the peptoid t-BuO$_2$CCH$_2$N(Bn)COCH$_2$N(C$_4$H$_8$NHCBz)COCH$_2$NFMOC(Bn) synthesized from HO$_2$CCH$_2$N(C$_4$H$_8$NHCBz)COCH$_2$NFMOC(Bn). One skilled in the art will appreciate that t-BuO$_2$CCH$_2$N(Bn)COCH$_2$N(C$_4$H$_8$NHCBz)COCH$_2$NFMOC(Bn) is merely an illustrative peptoid, and that other peptoids may be synthesized in accordance with the present disclosure.

i-Pr$_2$NEt (about 0.83 mL, about 4.8 mmol, 1.1 eq.) was added to a solution of HO$_2$CCH$_2$N(C$_4$H$_8$NHCBz)COCH$_2$NFMOC(Bn) (about 2.8 g, about 4.3 mmol, 1.0 eq.) in CH$_2$Cl$_2$ (about 10 mL) contained in a RBF (e.g., a 50 mL RBF), followed by addition of PyBrOP (about 2.0 g, about 4.3 mmol, 1.0 eq.). The resulting solution was stirred for about 10 minutes. Then, a solution of t-BuO$_2$CCH$_2$NHBn (about 1.25 g, about 5.6 mmol, 1.3 eq.) in CH$_2$Cl$_2$ (about 7.0 mL) was added, resulting in a limiting reactant concentration of about 0.25 M. The resulting reaction mixture was stirred overnight under argon. The solvent was then evaporated and the resulting residue was diluted with saturated aqueous NaHCO$_3$ solution (about 50 mL). The resulting mixture was extracted with EtOAc (about 150 mL, 3×50 mL), and the organic phase was washed with brine (about 50 mL), dried over Na$_2$SO$_4$, then filtered and concentrated into an oil. The resulting oil was dissolved in CH$_2$Cl$_2$ and loaded onto silica gel. The product was then purified by flash chromatography on silica gel, eluting with a gradient of EtOAc/hexanes. The resulting product containing fractions were concentrated and dried under high vacuum, yielding the product as a foam (about 3.3 g, about 88% yield).

HO$_2$CCH$_2$N(B*n*)COCH$_2$N(C$_4$H$_8$NHCB*z*) COCH$_2$NFMOC(B*n*)

Figure 17:
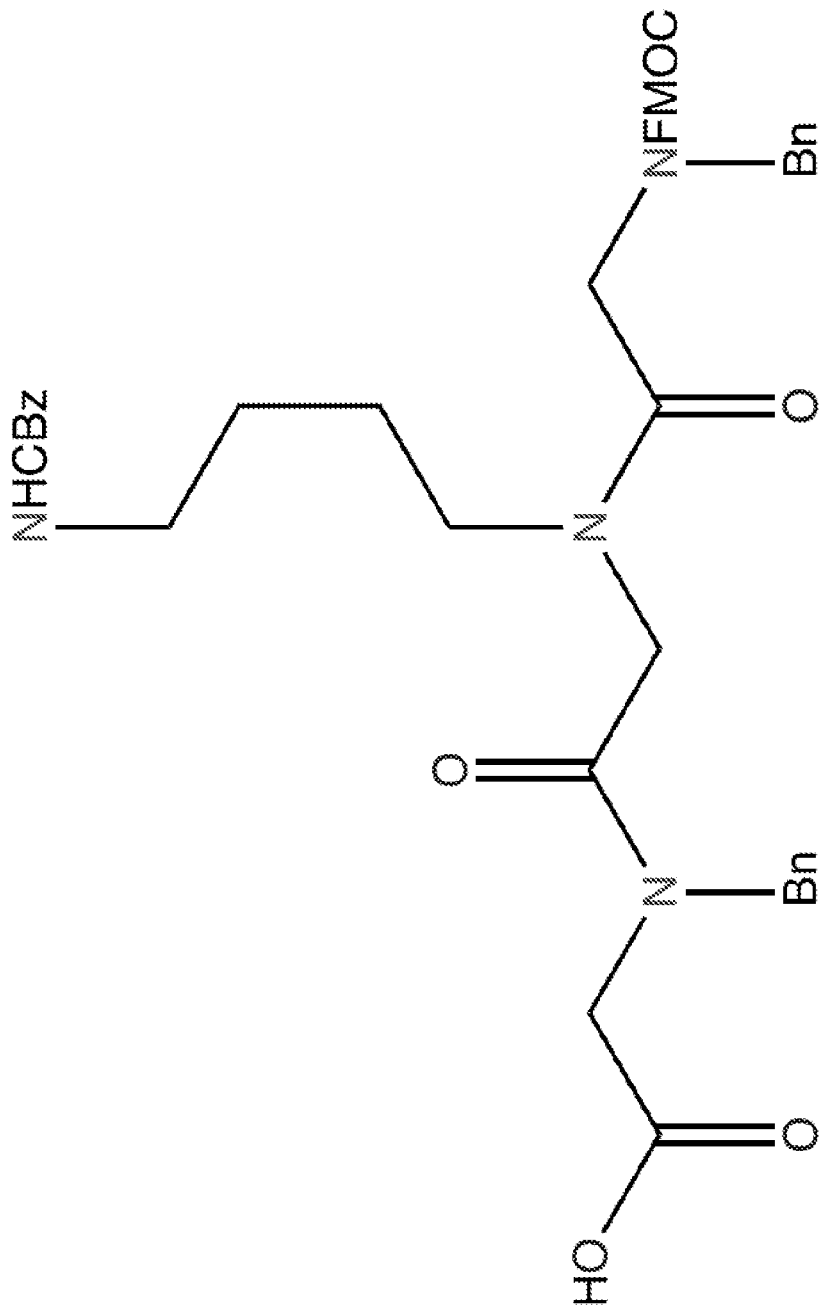
FIG. 17 is a chemical structure of the example peptoid of FIG. 16 altered to substitute t-Bu protective group with a hydrogen, in accordance with embodiments of the present disclosure.

FIG. 17 illustrates the peptoid HO$_2$CCH$_2$N(Bn)COCH$_2$N (C$_4$H$_8$NHCBz)COCH$_2$NFMOC(Bn) synthesized from t-BuO$_2$CCH$_2$N(Bn)COCH$_2$N(C$_4$H$_8$NHCBz) COCH$_2$NFMOC(Bn). One skilled in the art will appreciate that HO$_2$CCH$_2$N(Bn)COCH$_2$N(C$_4$H$_8$NHCBz) COCH$_2$NFMOC(Bn) is merely an illustrative peptoid, and that other peptoids may be synthesized in accordance with the present disclosure.

i-Pr$_3$SiH (about 3.9 mL, about 19 mmol, 5.0 eq.) was added to a RBF (e.g., a 100 mL RBF) containing t-BuO$_2$CCH$_2$N(Bn)COCH$_2$N(C$_4$H$_8$NHCBz) COCH$_2$NFMOC(Bn) (about 3.3 g, about 3.8 mmol, 1.0 eq.), followed by addition of TFA (about 15 mL, about 0.25 M) and CH$_2$Cl$_2$ (about 5 mL). The resulting mixture was stirred for about 1 hr and 20 mins and then concentrated to dryness. The crude product was dissolved in CH$_2$Cl$_2$ and loaded onto silica gel. The product was then purified by flash chromatography on silica, eluting with EtOAc/hexanes. The product containing fractions were collected, concentrated, and dried under high vacuum, yielding the product as a foam (about 1.8 g, about 58% yield).

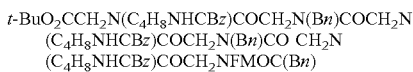
t-BuO$_2$CCH$_2$N(C$_4$H$_8$NHCB*z*)COCH$_2$N(B*n*)COCH$_2$N (C$_4$H$_8$NHCB*z*)COCH$_2$N(B*n*)CO CH$_2$N (C$_4$H$_8$NHCB*z*)COCH$_2$NFMOC(B*n*)

Figure 18:
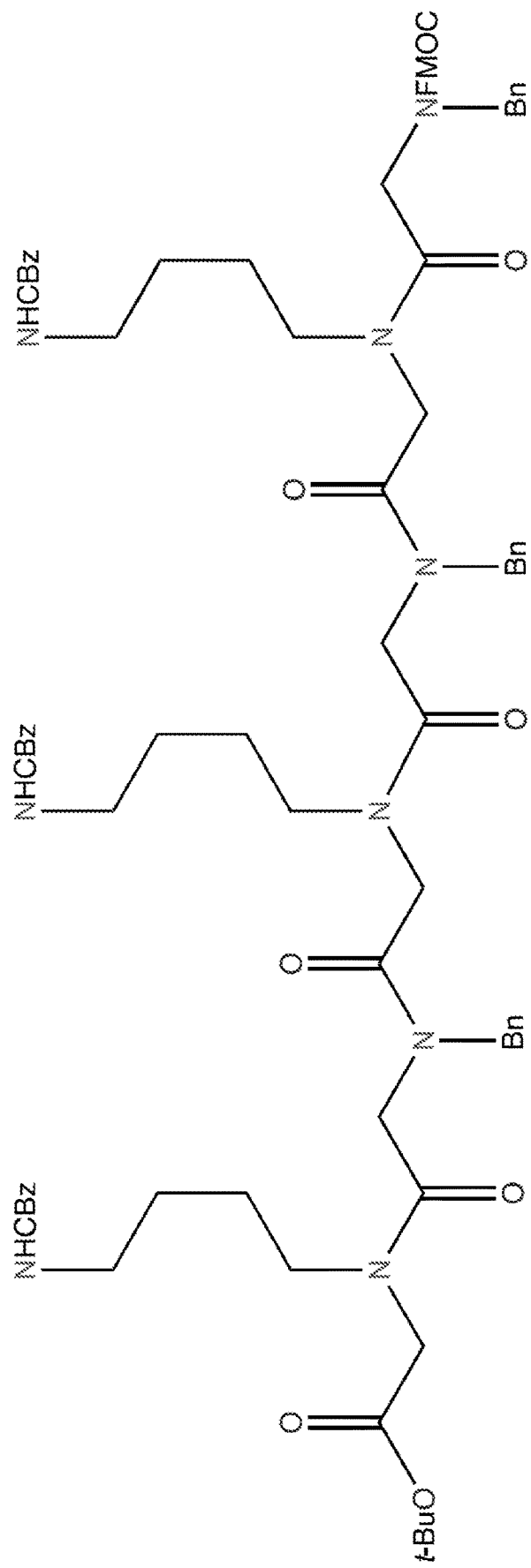
FIG. 18 is a chemical structure of the example peptoid of FIG. 17 altered to substitute a hydroxyl group with t-BuO$_2$CCH$_2$N(C$_4$H$_8$NHCBz)COCH$_2$N(Bn) COCH$_2$N—(C$_4$H$_8$NHCBz), in accordance with embodiments of the present disclosure.

FIG. 18 illustrates the peptoid t-BuO$_2$CCH$_2$N (C$_4$H$_8$NHCBz)COCH$_2$N(Bn)COCH$_2$N(C$_4$H$_8$NHCBz) COCH$_2$N(Bn)CO CH$_2$N(C$_4$H$_8$NHCBz)COCH$_2$NFMOC (Bn) synthesized from HO$_2$CCH$_2$N(Bn)COCH$_2$N (C$_4$H$_8$NHCBz)COCH$_2$NFMOC(Bn). One skilled in the art will appreciate that t-BuO$_2$CCH$_2$N(C$_4$H$_8$NHCBz)COCH$_2$N (Bn)COCH$_2$N(C$_4$H$_8$NHCBz)COCH$_2$N(Bn)CO CH$_2$N (C$_4$H$_8$NHCBz)COCH$_2$NFMOC(Bn) is merely an illustrative peptoid, and that other peptoids may be synthesized in accordance with the present disclosure.

i-Pr$_2$NEt (about 0.46 mL, about 2.7 mmol, 1.2 eq.) and PyBrOP (about 1.1 g, about 2.4 mmol, 1.1 eq.) were added to a solution of HO$_2$CCH$_2$N(Bn)COCH$_2$N(C$_4$H$_8$NHCBz) COCH$_2$NFMOC(Bn) (about 1.76 g, about 2.2 mmol, 1.0 eq.) in CH$_2$Cl$_2$ (about 10 mL) contained in a RBF (e.g., a 50 mL RBF) under argon. The resulting solution was stirred for about 10 minutes. A solution of t-BuO$_2$CCH$_2$N (C$_4$H$_8$NHCBz)COCH$_2$N(Bn)COCH$_2$NH(C$_4$H$_8$NHCBz) (about 1.6 g, about 2.2 mmol, 1.0 eq.) in CH$_2$Cl$_2$ (about 12 mL) was then added, producing an initial limiting reactant concentration of about 0.1 M. The resulting solution was stirred at rt overnight and the solvent was then evaporated. The residue was then dissolved in EtOAc (about 50 mL), and washed with saturated aqueous NaHCO$_3$ solution (about 50 mL). The aqueous phase was then extracted with EtOAc (about 100 mL, 2×50 mL). The combined organic phase was then washed with brine (about 50 mL), dried over Na$_2$SO$_4$, filtered, and concentrated. The resulting material was then dissolved in CH$_2$Cl$_2$, loaded onto silica gel and purified via flash chromatography on silica using a gradient of EtOAc/hexanes. The resulting product containing fractions were concentrated, and dried under high vacuum, yielding a foam (about 2.96 g, about 89% yield).

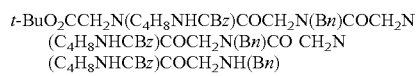
t-BuO$_2$CCH$_2$N(C$_4$H$_8$NHCB*z*)COCH$_2$N(B*n*)COCH$_2$N (C$_4$H$_8$NHCB*z*)COCH$_2$N(B*n*)CO CH$_2$N (C$_4$H$_8$NHCB*z*)COCH$_2$NH(B*n*)

Figure 19:
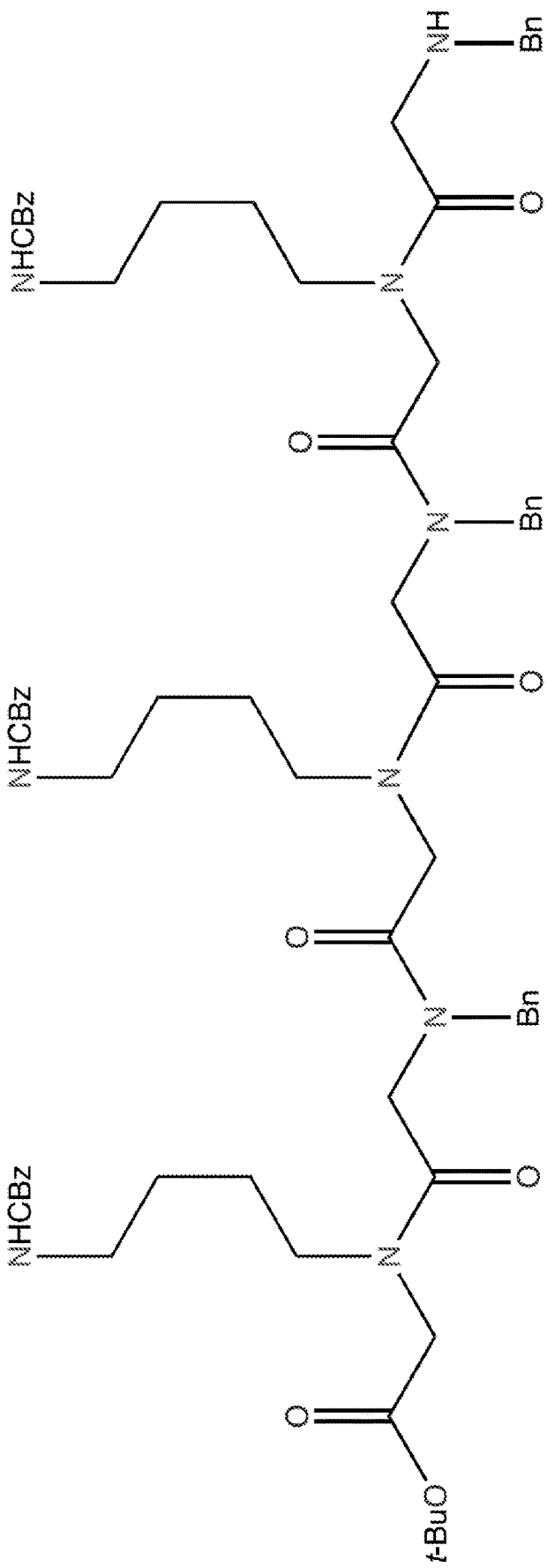
FIG. 19 is a chemical structure of the example peptoid of FIG. 18 altered to substitute an FMOC protective group with a hydrogen, in accordance with embodiments of the present disclosure.

FIG. 19 illustrates the peptoid t-BuO$_2$CCH$_2$N (C$_4$H$_8$NHCBz)COCH$_2$N(Bn)COCH$_2$N(C$_4$H$_8$NHCBz) COCH$_2$N(Bn)COCH$_2$N(C$_4$H$_8$NHCBz)COCH$_2$NH(Bn) synthesized from t-BuO$_2$CCH$_2$N(C$_4$H$_8$NHCBz)COCH$_2$N (Bn)COCH$_2$N(C$_4$H$_8$NHCBz)COCH$_2$N(Bn)CO CH$_2$N (C$_4$H$_8$NHCBz)COCH$_2$NFMOC(Bn). One skilled in the art will appreciate that t-BuO$_2$CCH$_2$N(C$_4$H$_8$NHCBz)COCH$_2$N (Bn)COCH$_2$N(C$_4$H$_8$NHCBz)COCH$_2$N(Bn)COCH$_2$N (C$_4$H$_8$NHCBz)COCH$_2$NH(Bn) is merely an illustrative peptoid, and that other peptoids may be synthesized in accordance with the present disclosure.

20% piperidine in THF (about 40 mL) was added to a solution of t-BuO$_2$CCH$_2$N(C$_4$H$_8$NHCBz)COCH$_2$N(Bn) COCH$_2$N(C$_4$H$_8$NHCBz)COCH$_2$N(Bn)COCH$_2$N (C$_4$H$_8$NHCBz)COCH$_2$NFMOC(Bn) (about 2.96 g, about 1.9 mmol, 1.0 eq.) in THF (about 10 mL). A white colored solid precipitated from the reaction mixture. After about 0.5 hr, the reaction appeared to be complete via TLC. The reaction mixture was then concentrated to dryness and evaporated with several small portions of toluene. The resulting product was dissolved in wet acetonitrile (MeCN) and stirred with several portions of hexanes. The MeCN layer was concentrated to dryness, dissolved in CH$_2$Cl$_2$ and loaded onto silica gel. The product was then purified via flash chromatography on silica, eluting first with a gradient of EtOAc/hexanes, then a gradient of MeOH/EtOAc. The resulting product containing fractions were collected, concentrated, and dried under high vacuum, resulting in about 2.3 g of product (about 91% yield).

HO$_2$CCH$_2$N(C$_4$H$_8$NHCB*z*)COCH$_2$N(B*n*)COCH$_2$N (C$_4$H$_8$NHCB*z*)COCH$_2$N(B*n*)CO CH$_2$N (C$_4$H$_8$NHCB*z*)COCH$_2$NH(B*n*)

Figure 20:
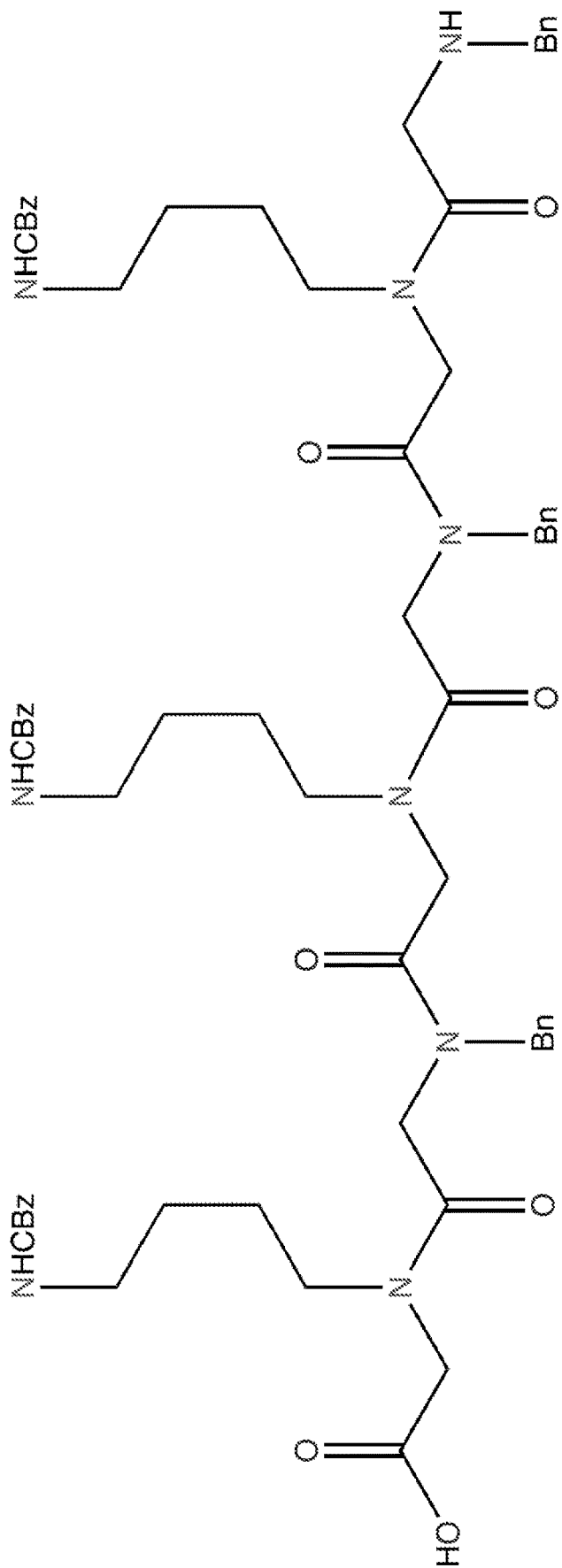
FIG. 20 is a chemical structure of the example peptoid of FIG. 19 altered to substitute a t-Bu protective group with a hydrogen, in accordance with embodiments of the present disclosure.

FIG. 20 illustrates the peptoid HO$_2$CCH$_2$N (C$_4$H$_8$NHCBz)COCH$_2$N(Bn)COCH$_2$N(C$_4$H$_8$NHCBz) COCH$_2$N(Bn)CO CH$_2$N(C$_4$H$_8$NHCBz)COCH$_2$NH(Bn) synthesized from t-BuO$_2$CCH$_2$N(C$_4$H$_8$NHCBz)COCH$_2$N (Bn)COCH$_2$N(C$_4$H$_8$NHCBz)COCH$_2$N(Bn)COCH$_2$N (C$_4$H$_8$NHCBz)COCH$_2$NH(Bn). One skilled in the art will appreciate that HO$_2$CCH$_2$N(C$_4$H$_8$NHCBz)COCH$_2$N(Bn) COCH$_2$N(C$_4$H$_8$NHCBz)COCH$_2$N(Bn)CO CH$_2$N (C$_4$H$_8$NHCBz)COCH$_2$NH(Bn) is merely an illustrative peptoid, and that other peptoids may be synthesized in accordance with the present disclosure.

i-Pr$_3$SiH (about 0.39 mL, about 1.9 mmol, 5.0 eq.) was added to a solution of t-BuO$_2$CCH$_2$N(C$_4$H$_8$NHCBz) COCH$_2$N(Bn)COCH$_2$N(C$_4$H$_8$NHCBz)COCH$_2$N(Bn) COCH$_2$N(C$_4$H$_8$NHCBz)COCH$_2$NH(Bn) (about 0.50 g, about 0.38 mmol, 1.0 eq.) in CH$_2$Cl$_2$ (about 2.0 mL), followed by addition of TFA (about 1.5 mL, about 0.25 M). The resulting solution was stirred at rt for about 2 hrs and then concentrated to dryness. The resulting residue was evaporated several times with toluene to remove residual TFA. The resulting material was dried under high vacuum overnight. The product was purified via reverse phase Biotage flash chromatography, running a gradient of 10-80% MeOH/H$_2$O on a C18 column. Product containing fractions were collected, concentrated, and dried under high vacuum, yielding about 0.40 g of product as a solid (about 83% yield).

Cyclic Hexamer

Figure 21:
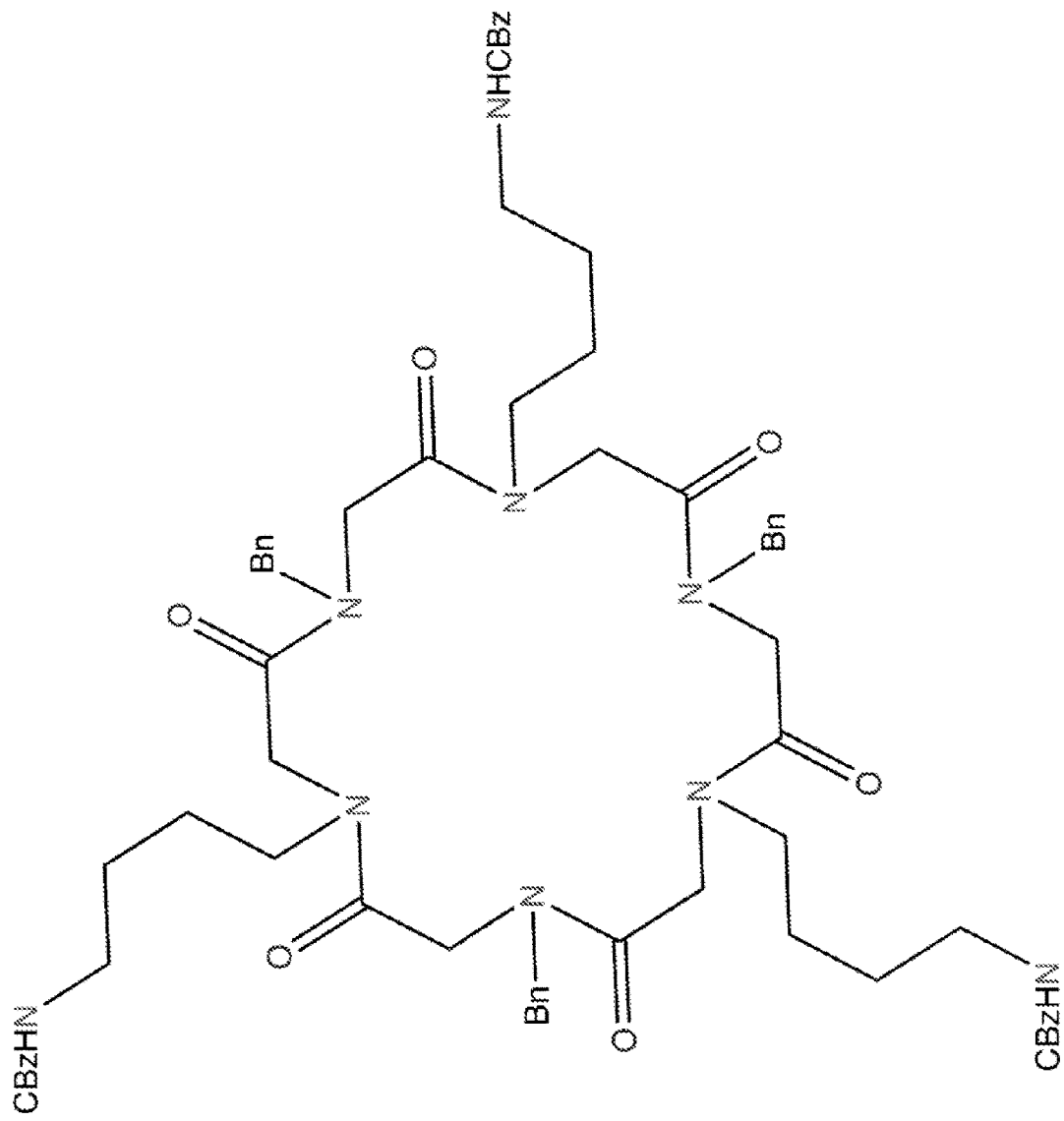
FIG. 21 is a chemical structure of a cyclic hexamer, in accordance with embodiments of the present disclosure.

FIG. 21 illustrates an example cyclic hexamer according to the present disclosure. To a solution of 1-(2-mesitylenesulfonyl)-3-nitro-1H-1,2,4-triazole (MSNT) (about 0.122 g, about 0.41 mmol, 5.0 eq.) in CH$_2$Cl$_2$ (about 71 mL) contained in a RBF (e.g., a 100 mL RBF) under Ar, was added a solution of HO$_2$CCH$_2$N(C$_4$H$_8$NHCBz)COCH$_2$N(Bn)COCH$_2$N(C$_4$H$_8$NHCBz)COCH$_2$N(Bn)CO CH$_2$N(C$_4$H$_8$NHCBz)COCH$_2$NH(Bn) (about 0.101 g, about 0.081 mmol, 1.0 eq.), i-Pr$_2$NEt (about 0.14 mL, about 0.81 mmol, 10 eq.) in CH$_2$Cl$_2$ (about 10 mL) via syringe pump configured to release 0.5 mL/hr. Final reactant concentration was about 0.001 M. The reaction mixture was stirred for about 4 days and diluted with about 50 mL H$_2$O. The aqueous phase was extracted with CH$_2$Cl$_2$ (about 50 mL, 2×25 mL). The combined organic phase was washed with H$_2$O (about 50 mL), then evaporated to dryness. The resulting product was then dried under high vacuum. Purification was achieved by reverse phase Biotage chromatography on a C$_{18}$ column, eluting with a gradient of 70-100% MeCN/H$_2$O. The product containing fractions were collected, concentrated, and dried under high vacuum, but still were impure via TLC. The product was then loaded onto silica from CH$_2$Cl$_2$, and purified via flash chromatography on silica using a gradient of 0-10% MeOH/CH$_2$Cl$_2$. The product containing fractions were then collected, concentrated, and dried under high vacuum, yielding about 21 mg of product as a colorless glass (about 21% yield).

While in solution cyclization has been described, one skilled in the art will appreciate that other types of cyclization (e.g., solid stage synthesis or on resin) may be used.

CBZ Deprotected Cyclic Hexamer

Figure 22:
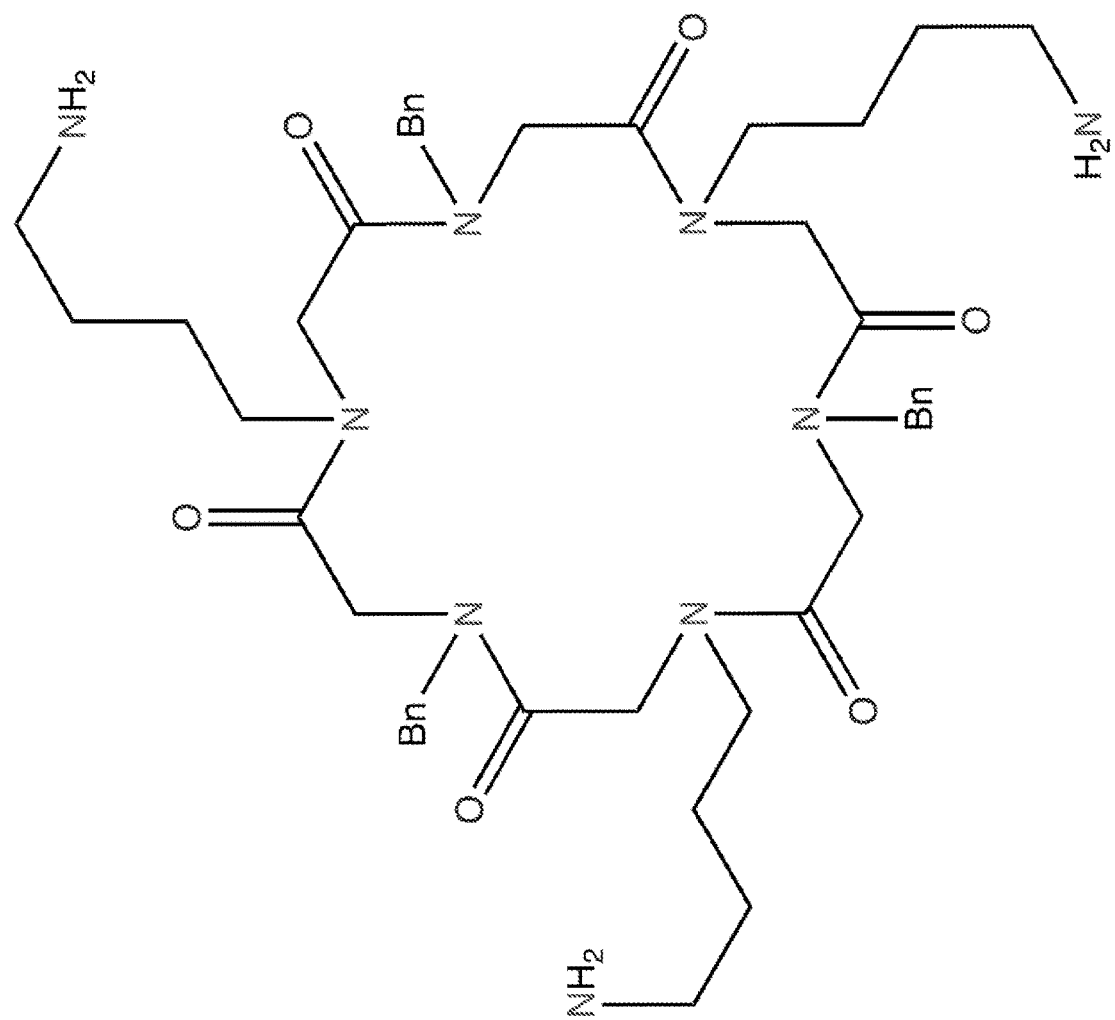
FIG. 22 is a chemical structure of a CBz deprotected cyclic hexamer, in accordance with embodiments of the present disclosure.

FIG. 22 illustrates an example CBz deprotected cyclic hexamer (i.e., an example cyclic peptoid-based chelating ligand) according to the present disclosure. To a solution of the foregoing cyclic hexamer (about 18 mg, about 0.015 mmol, 1.0 eq.) in EtOH (about 5 mL) contained in a RBF (e.g., a 15 mL RBF) fitted with a reflux condenser was added 10% Pd/C. The solution was heated to reflux and an about 0.3 M formic acid solution in EtOH (about 2.5 mL, about 0.74 mmol, 50 eq.) was added. After refluxing for about 0.5 hr, the reaction was determined to be complete via mass spectrometry. The mixture was filtered to remove Pd/C and evaporated to dryness. Purification was achieved via reverse phase Biotage chromatography on a C18 column, and eluted with a gradient of 20-100% MeCN/H$_2$O. Product containing fractions were concentrated, yielding the product as a white colored solid after drying under high vacuum (about 12 mg, about 56% yield).

Protected Catechol Ester

Figure 23:
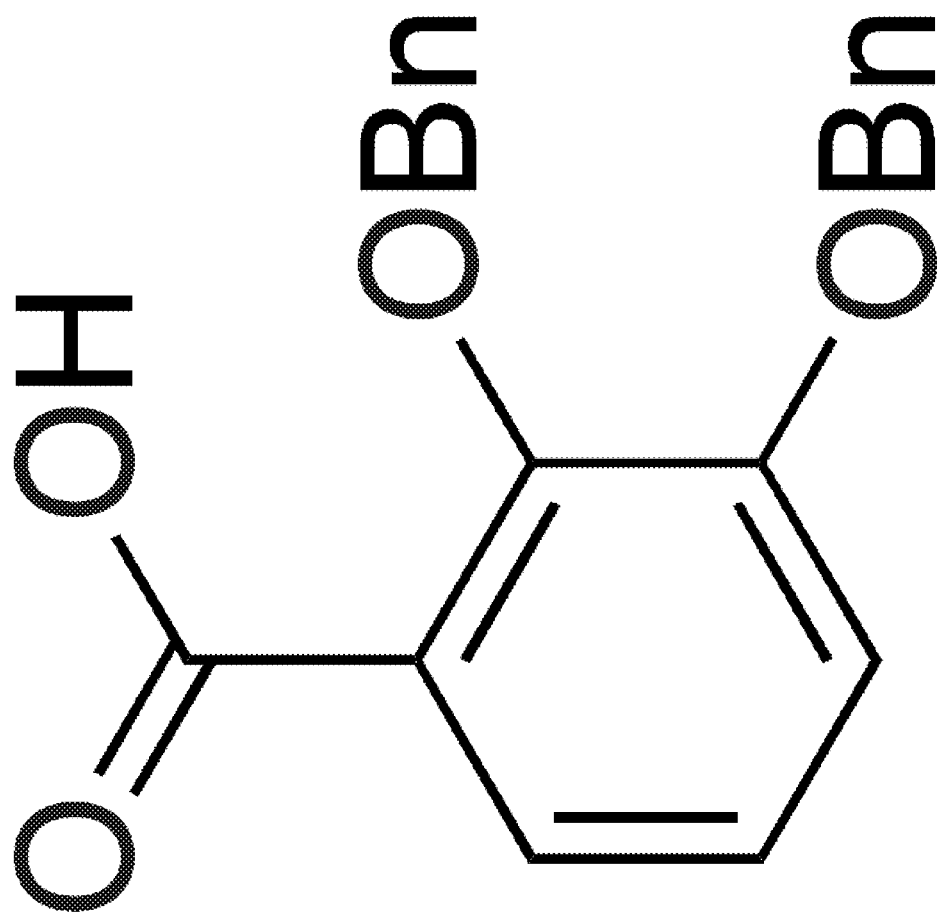
FIG. 23 is a chemical structure of a protected catechol ester, in accordance with embodiments of the present disclosure.

FIG. 23 illustrates a chemical structure of a protected catechol ester. The following is an example for preparing the protected catechol ester of FIG. 23.

To a 500 mL RBF was added acetone (200 mL). The acetone was then degassed by sparging with Ar using a needle for 0.5 hr. 2,3-dihydroxybenzoic acid (1.0 g, 6.5 mmol, 1.0 eq.) was added, followed by K$_2$CO$_3$ (3.64 g, 26.4 mmol, 4.1 eq.) and benzyl bromide (4.7 mL, 39.5 mmol, 6.1 eq.). A reflux condenser was attached, and the RBF was flushed with Ar and heated to reflux with stirring. The solution was refluxed for 24 hrs, cooled to rt, and filtered from solids. The resulting solids were washed with acetone. The solution was concentrated to dryness and excess benzyl bromide removed under high vacuum overnight. The resulting oil was purified via Biotage flash chromatography on a silica gel column, eluting with a gradient of EtOAc/hexanes. The product containing fractions were concentrated, yielding a colorless oil that was dried under high vacuum. The oil gradually crystallized (2.59 g, 94%).

Protected Catechol Acid

Figure 24:
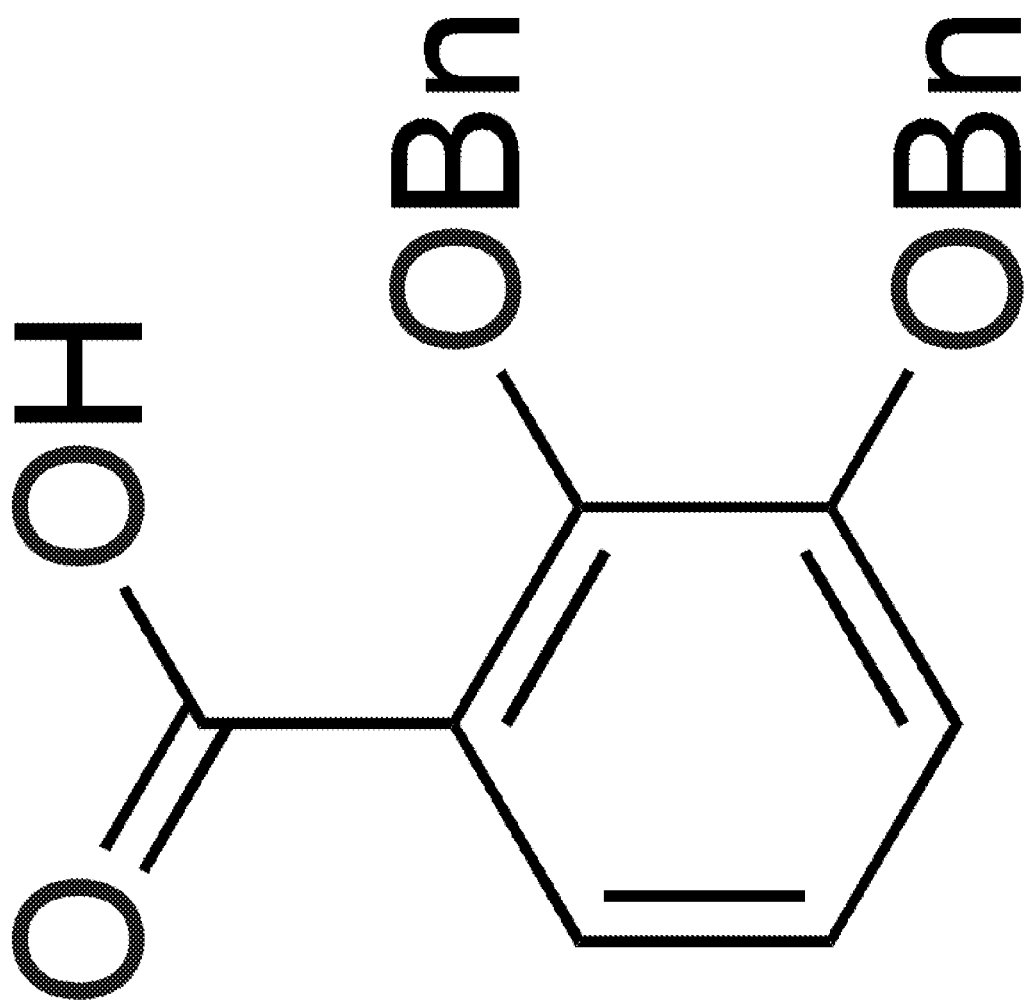
FIG. 24 is a chemical structure of a protected catechol acid, in accordance with embodiments of the present disclosure.

FIG. 24 illustrates a chemical structure of a protected catechol acid produced from the protected catechol ester of FIG. 23. The following is an example for preparing the protected catechol acid of FIG. 24 from the protected catechol ester of FIG. 23.

To a solution of the protected catechol ester of FIG. 23 (2.54 g, 5.98 mmol, 1.0 eq.) in MeOH (360 mL) contained in a 1000 mL RBF was added aqueous NaOH, 5N (90 mL, 75 eq.). A reflux condenser was attached and the reaction apparatus was flushed with Ar. The reaction mixture was refluxed for 4 hrs, cooled to rt, and excess MeOH was evaporated. H$_2$O (100 mL) was then added and the mixture was extracted with Et$_2$O (2×100 mL). The aqueous layer was acidified with 12 N aqueous HCl until a white precipitate formed, pH 4.0. EtOAc was added, the aqueous layer was saturated with NaCl, and extracted with EtOAc (2×50 mL). The combined organic phase was dried over Na$_2$SO$_4$, filtered, and concentrated to dryness, yielding a white solid. Product was dissolved in CH$_2$Cl$_2$/hexanes, CH$_2$Cl$_2$ was evaporated, and the resulting solution was chilled in a freezer overnight, then filtered and washed with hexanes, and dried under vacuum (1.88 g, 94%).

Protected Catechol Acid Chloride

Figure 25:
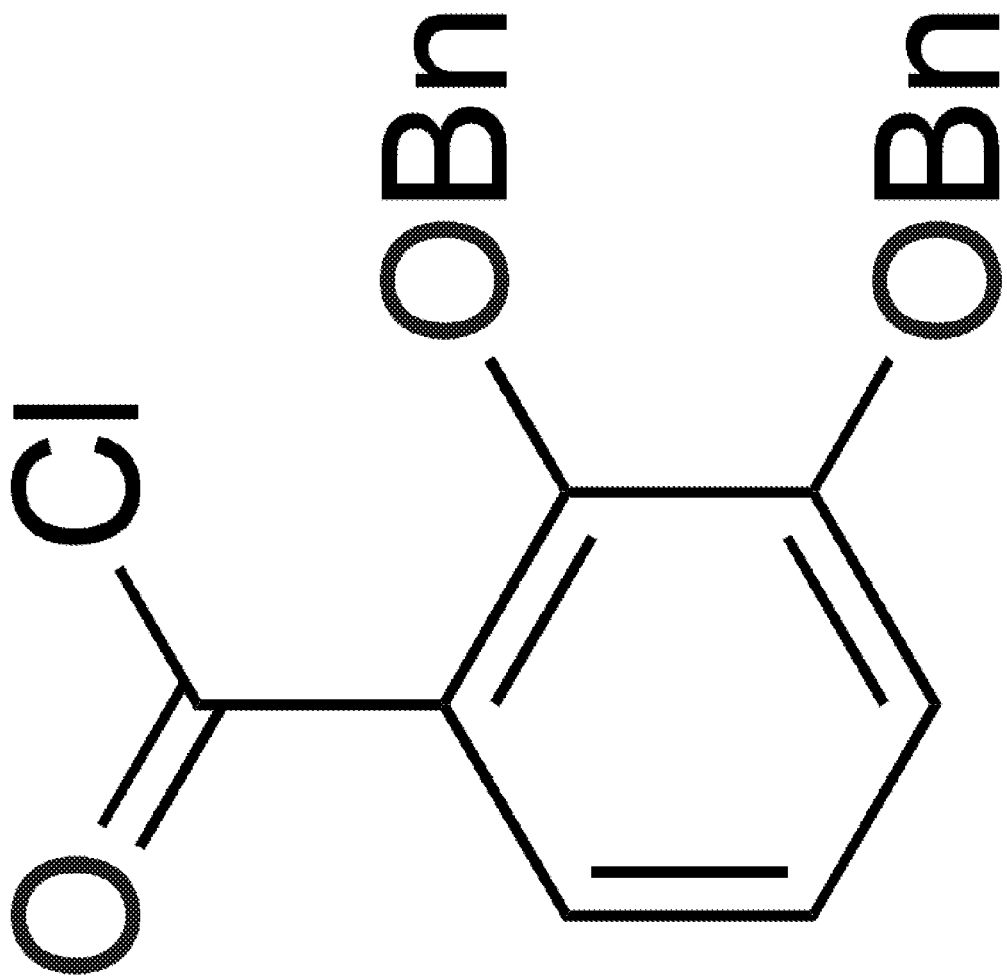
FIG. 25 is a chemical structure of a protected catechol acid chloride, in accordance with embodiments of the present disclosure.

FIG. 25 illustrates a chemical structure of a protected catechol acid chloride produced from the protected catechol acid of FIG. 24. The following is an example for preparing the protected catechol acid chloride of FIG. 25 from the protected catechol acid of FIG. 24.

Thionyl chloride was freshly distilled under Ar prior to use. To a 15 mL RBF containing the protected catechol acid of FIG. 24 (0.25 g, 0.75 mmol, 1.0 eq.) was attached to a reflux condenser. The RBF was then flushed with Ar. SOCl$_2$ (4 mL, 55 mmol, 74 eq.) was added. The reaction mixture was heated with stirring under Ar. After refluxing for 3 hrs, the reaction mixture was cooled to rt and the excess SOCl$_2$ was evaporated under high vacuum, yielding a pink colored oil that solidified after standing (229 mg, 88%).

Cyclic Hexamer Including Protected Catecholate Functionality

In at least some examples, catecholate may be substituted for a hydrogen on a primary amine forming a terminal functional group of a side chain of a deprotected cyclic hexamer. For example, the oxygen, of a hydroxyl group of a carboxylic acid of catecholate, may be bonded to the nitrogen of a primary amine. The following is an example for preparing the cyclic hexamer of FIG. 26 from the cyclic hexamer of FIG. 22 and the protected catechol acid chloride of FIG. 25.

To a solution of the protected catechol acid chloride of FIG. 25 (161 mg, 0.48 mmol, 18.0 eq.) and oxyma (104 mg 0.73 mmol, 27.0 eq.) in DMF (1.0 mL) contained in a 5 mL RBF was added DIC (114 uL, 0.73 mmol, 27.0 eq.) dropwise. The resulting yellow colored solution was stirred under Ar for 15 min. To a 5 mL Biotage microwave vial containing a stir bar was added the triamine cyclic hexamer of FIG. 22 (25 mg, 0.027 mmol, 1.0 eq.). Et$_3$N (67 uL, 0.48 mmol, 18 eq.) was added to the microwave vial, followed by the solution of activated catechol acid. DMF (1.0 mL) was used to complete the transfer of the activated acid. The microwave vial was sealed and the resulting orange colored reaction mixture was heated in a Biotage Initiator microwave reactor (75° C., 1 hr). Volatiles were then removed by azeotropic distillation with toluene using a rotary evaporator. The resulting residue was dissolved in $CH_2Cl_2$ (50 mL) and washed with saturated aqueous $NaHCO_3$ solution (50 mL). The aqueous phase was then extracted with $CH_2Cl_2$ (2×25 mL). The combined organic phases were then washed with saturated aqueous $NaHCO_3$ solution (50 mL), brine (50 mL) and dried over $Na_2SO_4$. The solution was then filtered and evaporated to dryness. The product was purified 2× by RP C-18 Biotage chromatography on a 30 g column, 50-100% acetonitrile/$H_2O$ 0.5% formic acid additive in the acetonitrile. The product was isolated as an oil (43 mg, 92%). RP HPLC indicated some impurities. A partial separation by analytical TLC was obtained using silica gel plates, 10% MeOH/$CH_2Cl_2$ 1% AcOH additive.

Cyclic Hexamer Including Protected Catecholate Functionality

In at least some examples, protected catecholate functionality of a cyclic hexamer may be deprotected by substituting benzyl groups (Bn) with hydrogen, resulting in the formation of hydroxyl groups. The following is an example for preparing the cyclic hexamer of FIG. 27 from the cyclic hexamer of FIG. 26.

Figure 26:
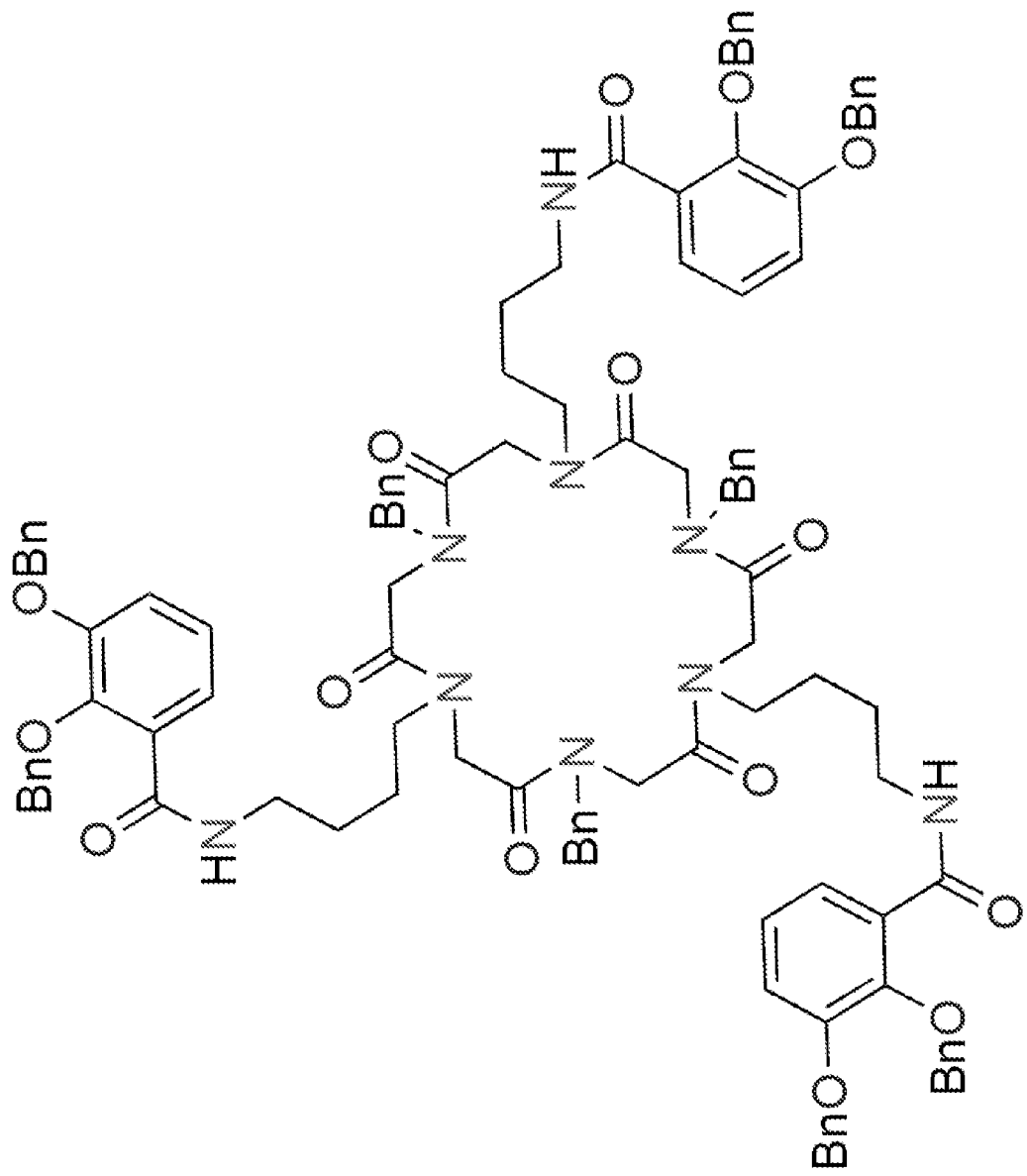
FIG. 26 is a chemical structure of a cyclic hexamer including catecholate functionality, in accordance with embodiments of the present disclosure.

To a solution of the cyclic hexamer of FIG. 26 (including protected catecholate functionality) (38 mg, 0.021 mmol, 1.0 eq.) in ethanol (20 mL) in a 100 mL Teflon RBF was added Pd/C 10% Pd (15 mg, 40% by weight). The reaction apparatus was flushed with Ar and then flushed with $H_2$. The reaction mixture was vigorously stirred under an atmosphere of $H_2$ provided by a balloon. After stirring for 26 hrs, the mixture was filtered through a 0.2 um Teflon syringe filter and the filter was washed with ethanol (3×5 mL). The combined ethanol phase was evaporated to dryness in a Teflon RBF. Purification by RP C-18 Biotage chromatography was attempted using a gradient of 40-100% MeCN/$H_2O$, MeCN contained 0.5% formic acid as an additive. Some of the product ran off the column initially within the $1^{st}$ column volume, while the remainder eluted as a broad hump during the gradient run.

Iron Affinity

Figure 27:
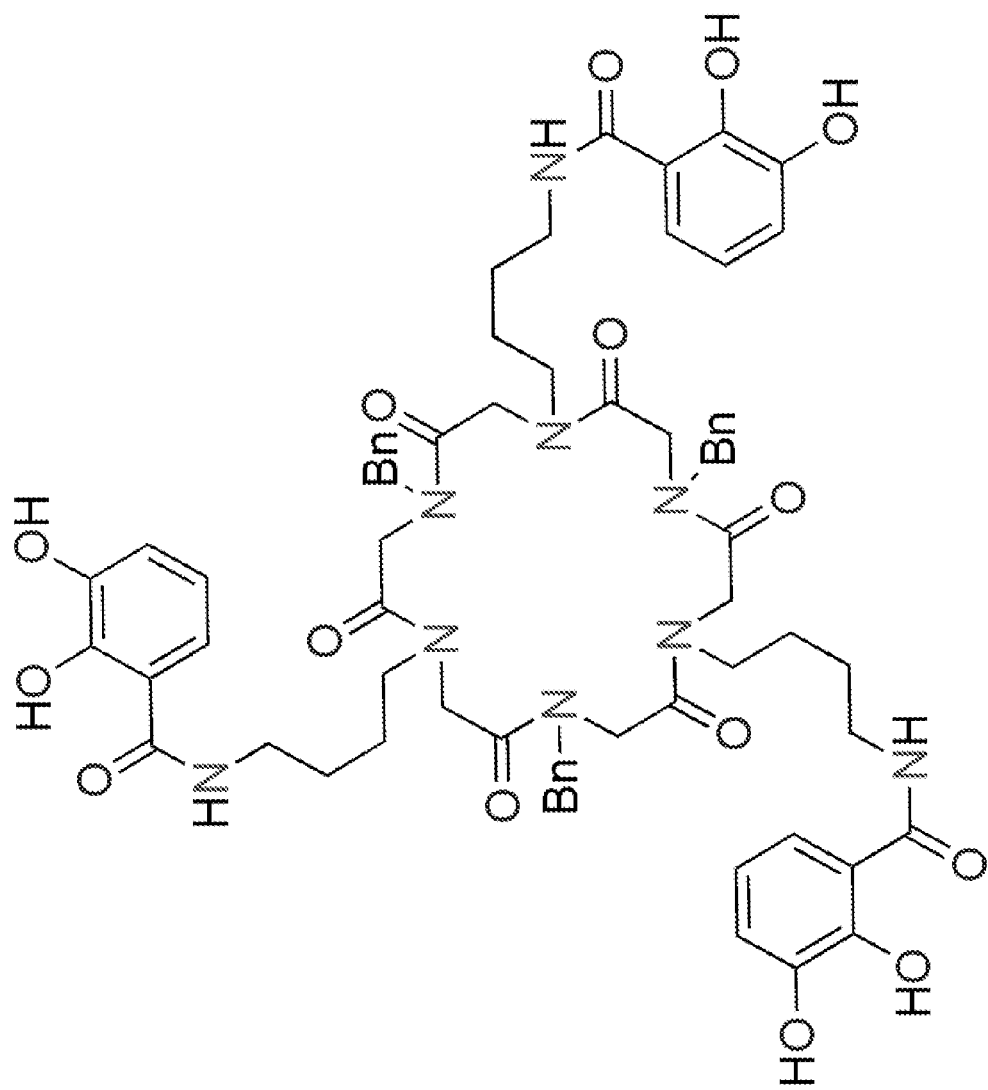
FIG. 27 is a chemical structure of a deprotected cyclic hexamer including catecholate functionality, in accordance with embodiments of the present disclosure.
Figure 28:
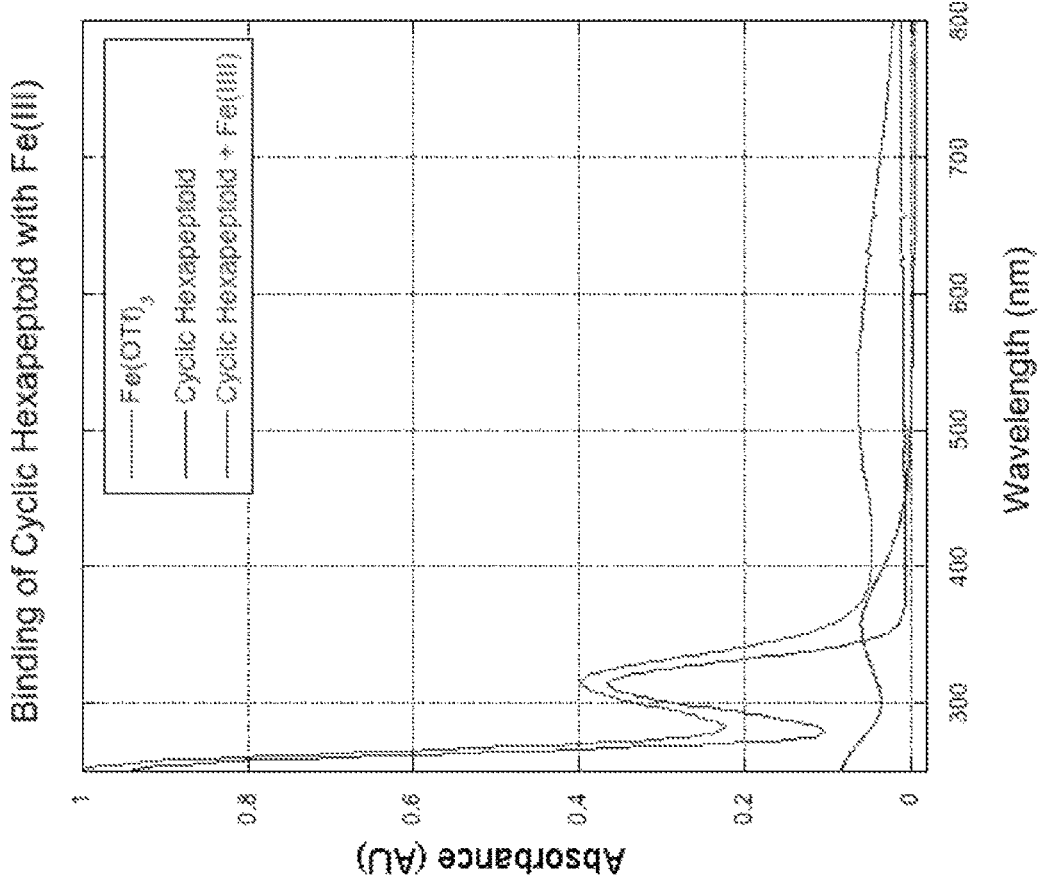
FIG. 28 is UV-visible spectroscopy spectra showing Fe(III) binding of the cyclic hexamer of FIG. 27, in accordance with embodiments of the present disclosure.

Ability of the cyclic hexamer of FIG. 27 to bind Fe(III) was demonstrated by UV-visible spectroscopy. Solutions of the cyclic hexamer, Fe(III) triflate, and a solution of equal parts cyclic hexamer and Fe(III) triflate in methanol were prepared and examined by UV-visible spectroscopy. The solution of Fe(III) cyclic hexamer showed a broad absorbance band centered around 521 nm (see FIG. 28).

Overview of Terms and Abbreviations

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the foregoing detailed description and the claims.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that can depend on the desired properties sought and/or limits of detection under standard test conditions/methods.

While the present disclosure has been particularly described in conjunction with specific embodiments, it is evident that many alternatives, modifications, and variations will be apparent to those skilled in the art in light of the foregoing description. It is therefore contemplated that the appended claims will embrace any such alternatives, modifications, and variations as falling within the true spirit and scope of the present disclosure.

What is claimed is:

1. A method of producing a peptoid-based chelating ligand, comprising:
    obtaining a peptoid backbone comprising a plurality of secondary amines, wherein at least a portion of the plurality of secondary amines is protected;
    deprotecting the at least a portion of the plurality of secondary amines; and
    attaching a side chain to at least a first deprotected secondary amine, the side chain comprising a functional group configured to form a coordinate bond with at least one hard cation.

2. The method of claim 1, wherein the functional group is phosphonate, catecholate, amine, guanidinium, phosphoramidate, n-acylhydroxyamines, N-hydroxypyridone, or carbamoylmethylphosphine oxide (CMPO).

3. The method of claim 1, wherein the at least one hard cation comprises at least one actinide.

4. The method of claim 1, wherein the at least one hard cation comprises at least one lanthanide.

5. The method of claim 1, wherein the side chain comprises at least one electron donor atom positioned between the peptoid backbone and the functional group, wherein the at least one electron donor atom comprises at least one of nitrogen, oxygen, or fluorine.

6. The method of claim 1, wherein the side chain comprises at least one electron donor group comprising sulfur.

7. The method of claim 6, wherein the at least one donor group comprising sulfur comprises at least one of a thiolate or a thiourea.

8. The method of claim 1, further comprising:
    attaching a second side chain to at least a second deprotected secondary amine, the second side chain comprising a second function group configured to form a second coordinate bond with the at least one hard cation; and
    attaching a third side chain to at least a third deprotected secondary amine, the third side chain comprising a third function group configured to form a third coordinate bond with the at least one hard cation.

9. The method of claim 8, wherein the at least one hard cation comprises a +3 charged actinide.

10. The method of claim 8, wherein the at least one hard cation comprises a +3 charged lanthanide.

11. The method of claim 1, wherein the peptoid backbone is cyclic.

* * * * *